US008124616B2

(12) United States Patent
Frechette

(10) Patent No.: US 8,124,616 B2
(45) Date of Patent: Feb. 28, 2012

(54) BICYCLIC PPAT INHIBITORS AS ANTIBACTERIAL AGENTS

(75) Inventor: Roger Frechette, Reading, MA (US)

(73) Assignee: Biota Scientific Management Pty Ltd, Victoria (AU)

( * ) Notice: Subject to any disclaimer, the term of this patent is extended or adjusted under 35 U.S.C. 154(b) by 355 days.

(21) Appl. No.: 12/324,347

(22) Filed: Nov. 26, 2008

(65) Prior Publication Data
US 2009/0203730 A1 Aug. 13, 2009

Related U.S. Application Data

(60) Provisional application No. 60/991,511, filed on Nov. 30, 2007.

(51) Int. Cl.
A61K 31/437 (2006.01)
A61K 31/4365 (2006.01)
C07D 471/04 (2006.01)
C07D 513/04 (2006.01)
C07D 495/04 (2006.01)
A61P 31/04 (2006.01)

(52) U.S. Cl. ......... 514/301; 514/303; 546/114; 546/118

(58) Field of Classification Search .......... 546/114, 546/118; 514/301, 303
See application file for complete search history.

(56) References Cited

U.S. PATENT DOCUMENTS

| 4,283,536 | A | 8/1981 | Kuehne et al. |
| 5,866,587 | A | 2/1999 | De Nanteuil et al. |
| 6,090,797 | A * | 7/2000 | Madsen et al. ............... 514/114 |
| 6,177,443 | B1 | 1/2001 | Madsen et al. |
| 6,350,757 | B1 | 2/2002 | Brion et al. |
| 6,573,272 | B1 | 6/2003 | Newlander et al. |
| 6,825,213 | B2 * | 11/2004 | Feller et al. ................... 514/307 |
| 2002/0091125 | A1 | 7/2002 | Hay et al. |
| 2003/0232850 | A1 | 12/2003 | Newlander et al. |
| 2005/0070570 | A1 | 3/2005 | Garcia et al. |
| 2005/0215614 | A1 | 9/2005 | Singh et al. |
| 2006/0069102 | A1 | 3/2006 | Leban et al. |
| 2006/0273819 | A1 | 12/2006 | Opperman et al. |

FOREIGN PATENT DOCUMENTS

| DE | 19928424 | | 12/2000 |
| GB | 1055203 | A | 1/1967 |
| IN | 170439 | | 3/1992 |
| JP | 2004137185 | * | 5/2004 |
| WO | WO 00/58307 | A2 | 10/2000 |
| WO | WO 00/72846 | A1 | 12/2000 |
| WO | WO 01/87038 | | 11/2001 |
| WO | WO 02-062339 | A1 | 8/2002 |
| WO | WO 02/064590 | A2 | 8/2002 |
| WO | WO 02/064591 | A2 | 8/2002 |
| WO | WO 03/099821 | A1 | 12/2003 |
| WO | WO 2004/096802 | | 11/2004 |
| WO | WO 2007/104557 | A2 | 9/2007 |
| WO | WO 2009/073534 | A3 | 6/2009 |
| WO | WO 2009/073545 | A3 | 6/2009 |
| WO | WO 2009/102377 | A3 | 8/2009 |

OTHER PUBLICATIONS

Kametani et al., Journal of Medicinal Chemistry (1972), 15(2), 203-4.*
Stocker et al., Journal of Organic Chemistry (1990), 55(10), 3370-3.*
Fayol et al., Organic Letters (2004), 6(1), 115-118.*
International Search Report re: PCT/US2008/084924 Jun. 8, 2009.
International Search Report re: PCT/US2008/084832 Sep. 9, 2009.
International Search Report re: PCT/US2008/084948 Jul. 16, 2009.
Ahsan, A. M., et al., "Reserpine Analogues: Synthesis of β-Carboline Derivatives," *J. Chem. Soc., Chem. Soc.* Letchworth, GB, 3928-3930 (1963).
Afseh, E. M., et al., "*Pictet-Spengler* Reactions of Tryptamine and Tryptophan with Cycloalkanones and Ketotic Mannich Bases," *Manatshefte fur Chemie*, 116: 851-855 (1985).
Jackowski, S., and Rock, C.O., "Metabolism of 4'-phosphopantetheine in *Escherichia coli*," *J. Bacteriol.*, 158: 115-120 (1984).
Jackowski, S., and Rock, C.O., "Regulation of Coenzyme A Biosynthesis," *J. Bacteriol.*, 148: 926-932 (1981).
Jaworek, D., et al., "Adenosine-5'-diphosphate and Adenosine-5'-monophosphate," *Methods of Enzymatic Analysis*, 4: 2127-2131 (1974).
Leslie, B., et al., "Antibacterial Anthranilates with a Novel Mode of Action." Presented at the 42$^{nd}$ Interscience Conference on Antimicrobial Agents and Chemotherapy (ICAAC), San Diego, California (2002).
Mayer, J. P., et al., "Application of the Pictet-Spengler Reaction in Combinatorial Chemistry," *Tetrahedron Letters*, 37: 5633-5636 (1996).
Peters, K. P., et al., "The Automatic Search for Ligand Binding Sites in Proteins of Known Three-Dimensional Structure Using Only Geometric Criteria," *J. Mol. Biol.*, 256: 201-213 (1996).
Tripathi, R.C., et al., "Synthesis and SAR Studies in 2-Substituted 1,2,3,4-tetrahydro-9H-pyrido-[3,4-b]indole-3-carboxylic acids—A New Class of Potent Antiulcer Agents," *Indian J. of Chem.*, 28B: 333-337 (1989).
Ungemach, F., et al., "General Method for the Assignment of Sterochemistry of 1,2-Disubstituted 1,2,3,4-Tetrahydro-β-Carbolines by Carbon-13 Spectroscopy," *J. Am. Chem. Soc.*, 102: 6976-6984 (1980).

(Continued)

*Primary Examiner* — D M Seaman
*Assistant Examiner* — Niloofar Rahmani
(74) *Attorney, Agent, or Firm* — McCarter & English, LLP; Elizabeth A. Hanley, Esq.; Yu Lu

(57) ABSTRACT

Disclosed are compounds of Formula I, pharmaceutical compositions comprising Formula I and methods of treating bacterial infections. The disclosed compounds are inhibitors of PPAT (phosphopantetheine adenyl transferase), and are useful in the treatment and prevention of diseases caused by bacteria, particularly bacteria dependent on PPAT, for example, species such *Escherichia coli, Helicobacter pylori, Staphyloccocus aureus*, and the like.

11 Claims, No Drawings

OTHER PUBLICATIONS

Zhao, L., et al., "Inhibitors of Phosphopantetheine Adenylyltransferase." Presented at the 42$^{nd}$ Interscience Conference on Antimicrobial Agents and Chemotherapy, (ICAAC), San Diego, California (2002).

Hagen, T., et al., "DDQ Oxidations in the Indole Area. Synthesis of 4-Alkoxy-β-carbolines Including the Natural Products Crenatine and 1-Methoxycanthin-6-one," *J. Org. Chem.*, 54(9): 2170-2178 (1989).

Wall, M.D. et al. "Evaluation of N-(phenylmethyl)-4-[5-(phenylmethyl)-4,5,6,7-tetrahydro-1H-imidazo[4,5-c]pyridin-4-yl]benzamide inhibitors of Mycobacterium tuberculosis growth", Bioorganic & medicinal chemistry letters, May 15, 2007, v.17 No. 10, pp. 2740-2744 See Scheme 1 and table 1.

Fayol, Aude, et al., "Synthesis of Polysubstituted 4,5,6,7-Tetrahydrofuro[2,3-c]pyridines by a Novel Multicomponent Reaction," Org. Lett., 2004, vol. 6, No. 1, pp. 115-118 See figures and schemes.

Seefeld, M. A. et al., 'Inhibitors of bacterial enoyl acyl carrier protein reductase (FabI): 2,9-disubstituted 1,2,3,4-tetrahydropyrido[3,4-b]indoles as potential antibacterial agents', Bioorganic & Medicinal Chemistry Letters, 11(17), pp. 2241-2244 (2001) See table 2.

Wang, Haishan et al., 'Synthesis and Evaluation of Tryprostatin B and Demethoxyfumitremorgin C Analogues', Journal of Medicinal Chemistry, 43(8), pp. 1577-1585 (2000) See the whole document.

* cited by examiner

BICYCLIC PPAT INHIBITORS AS ANTIBACTERIAL AGENTS

GOVERNMENT SUPPORT

This invention was made with government support from the National Institutes of Health. The government has certain rights in the invention.

RELATED APPLICATION

This application claims priority to U.S. Provisional Application No. 60/991,511, filed Nov. 30, 2007, entitled "BICYCLIC PPAT INHIBITORS AS ANTIBACTERIAL AGENTS." The contents of any patents, patent applications, and references cited throughout this specification are hereby incorporated by reference in their entireties.

TECHNICAL FIELD

The present invention relates to compositions which inhibit PPAT and methods and uses thereof.

BACKGROUND OF THE INVENTION

In the last century, antibiotics were developed that led to significant reductions in mortality. Unfortunately, widespread use has led to the rise of antibiotic resistant bacteria, e.g., methicillin resistant *Staphyloccocus aureus* (MRS A), vancomycin resistant *enterococci* (VRE), and penicillin-resistant *Streptococcus pneumonias* (PRSP). Some bacteria are resistant to a range of antibiotics, e.g., strains of *Mycobacterium tuberculosis* resist isoniazid, rifampin, ethambutol, streptomycin, ethionamide, kanamycin, and rifabutin. In addition to resistance, global travel has spread relatively unknown bacteria from isolated areas to new populations. Furthermore, there is the threat of bacteria as biological weapons. These bacteria may not be easily treated with existing antibiotics.

Infectious bacteria employ the coenzyme A (CoA) biosynthesis pathway, and, particularly in the penultimate step of the pathway, depend on phosphopantetheine adenyl transferase (PPAT), which transfers an adenyl moiety from adenosine triphosphate (ATP) to 4'-phosphopanthetheine, forming dephospho-CoA (dPCoA). While PPAT is present in mammalian cells, bacterial and mammalian PPAT enzymes differ substantially in primary sequence (about 18% identity) and physical properties. Thus, PPAT presents a desirable, selective target for new antibiotics.

Recent efforts have resulted in the identification of compounds which inhibit *E. coli* PPAT (Leslie, et al. "Antibacterial Anthranilates with a Novel Mode of Action"; Zhao, et al. "Inhibitors of Phosphopantetheine Adenylyltransferase"; Presented at the 42nd Interscience Conference on Antimicrobial Agents and Chemotherapy (ICAAC), San Diego, Calif., 2002). However, these compounds are not appropriate for drug development. Furthermore, in one case, the structures are peptidic, while in the other case, representative compounds exhibited poor activity against purified PPAT.

Therefore, there is a need for new antibiotics that target PPAT, whereby infections from bacteria dependent on PPAT can be treated.

SUMMARY OF THE INVENTION

The present invention relates to certain bicyclic PPAT inhibitors. The disclosed compounds have antibiotic activity against bacteria, including drug-resistant bacteria. Thus, compounds that are PPAT inhibitors, methods of treatment with the disclosed PPAT inhibitors, and pharmaceutical compositions comprising the disclosed PPAT inhibitors are provided herein.

In one aspect, the invention provides a method of treating a subject for a bacterial infection, comprising administering to a subject in need of treatment for a bacterial infection an effective amount of a compound represented by structural Formula I:

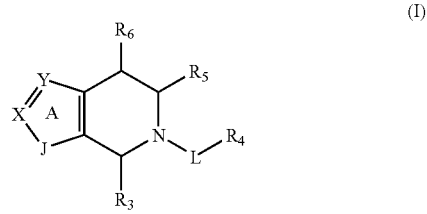

and pharmaceutically acceptable salts, solvates, hydrates, enantiomers, stereoisomers, rotamers, tautomers, diastereomers, or racemates thereof.

The invention is useful for treating (therapeutically or prophylactically) bacterial infections, particularly infections caused by bacteria that depend on the CoA biosynthesis pathway, and more particularly, infections caused by bacteria that express the PPAT enzyme. Furthermore, it is useful against bacteria that have developed antibiotic resistance, especially multiple drug resistant strains, because it is believed to act through a different mechanism than existing, widely used antibiotics.

DETAILED DESCRIPTION OF THE INVENTION

The invention is generally related to methods, compounds, and pharmaceutical compositions for treating and preventing bacterial infections. In particular, the invention relates to substituted bicyclic derivatives that are PPAT inhibitors.

In one embodiment, the invention is a method of treating a subject for a bacterial infection, comprising administering to a subject in need of treatment for a bacterial infection an effective amount of a compound represented by structural Formula I:

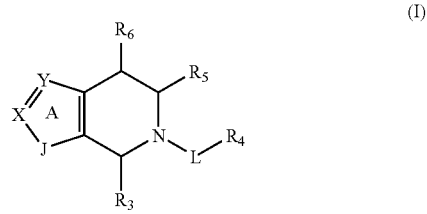

and pharmaceutically acceptable salts, solvates, hydrates, enantiomers, stereoisomers, rotamers, tautomers, diastereomers, or racemates thereof;

wherein ring A is optionally substituted at any substitutable ring atom;

X and Y are each, independently, —C— or —N—;

J is —O—, —S—, or —NR2-, wherein R2 is —H or optionally substituted C1-C5 alkyl;

or, J is —NR2'—, wherein R2' is optionally substituted aryl, aralkyl, heteroaryl, heteroaralkyl, C3-C7 cycloaliphatic, or C3-C7 cycloalkyl;

R3 is optionally substituted aryl, aralkyl, heteroaryl, heteroaralkyl, C3-C7 cycloaliphatic, or C3-C7 cycloalkyl;

L is —(CH$_2$)—, —(CO)—, —(CS)—, —(SO)—, or —(SO$_2$)—;

R4 is an aryl, biaryl, heteroaryl, biheteroaryl, heteroarylaryl, aryl-heteroaryl, aralkyl, heteroaralkyl, C1-C8 aliphatic, C3-C7 cycloalkyl, C5-C7 cycloaliphatic, or a 3-7 membered non-aromatic heterocyclic group;

wherein R4 can be substituted with halogen, —(CO)OR$^a$, —(CO)O(CO)R$^a$, —(CS)OR$^a$, —(SO)OR$^a$, SO$_3$R$^a$, —OSO$_3$R$^a$, —P(OR$^a$)$_2$, —(PO)(OR$^a$)$_2$, —O(PO)(OR$^a$)$_2$, —B(OR$^a$)$_2$, —(CO)NR$^b{}_2$, —NR$^c$(CO)R$^a$, —SO$_2$NR$^b{}_2$, or —NR$^c$SO$_2$R$^a$;

R5 is —H, —(CH$_2$)$_n$(CO)OR$^a$, —(CH$_2$)$_n$(CO)O(CO)R$^a$, —(CH$_2$)$_n$(CS)OR$^a$, —(CH$_2$)$_n$(SO)OR$^a$, (CH$_2$)$_n$SO$_3$R$^a$, —(CH$_2$)$_n$OSO$_3$R$^a$, —(CH$_2$)$_n$P(OR$^a$)$_2$, —(CH$_2$)$_n$(PO)(OR$^a$)$_2$, —(CH$_2$)$_n$O(PO)(OR$^a$)$_2$, —(CH$_2$)$_n$B(OR$^a$)$_2$, —(CH$_2$)$_n$(CO)NR$^b{}_2$, —(CH$_2$)$_n$NR$^c$(CO)R$^a$, —(CH$_2$)$_n$SO$_2$NR$^b{}_2$, or —(CH$_2$)$_n$NR$^c$SO$_2$R$^a$;

n is 0 to 5;

R6 is —H, —OH, halogen, or optionally substituted C1-C3 alkyl or alkoxy;

each R$^a$ and R$^c$ are, independently, —H, C1-C5 alkyl, aryl, or aralkyl;

each R$^b$ is, independently, —H, C1-C5 alkyl, aryl, or aralkyl, or NR$^b{}_2$ is a nonaromatic heterocyclic group.

In an exemplary embodiment, n is 0.

In one embodiment, ring A in structural Formula I is an optionally substituted heteroaryl group, for example, an optionally substituted furanyl, pyrrolyl, thienyl, oxazolyl, isooxazolyl, thiazolyl, isothiazolyl, or imidazolyl group.

Suitable optional substituents for substitutable ring atoms in Ring A are provided herein below in the section describing substituents for aryl and heteroaryl groups. More preferably, Ring A is optionally, independently, substituted at any substitutable ring atom with R1. Each R1 are, independently, halogen, —CN, —NO$_2$, —CF$_3$, —OCF$_3$, —OR$^d$, —(CO)R$^d$, —(CO)OR$^d$, —O(CO)R$^d$, —(CO)O(CO)R$^d$, —(CS)OR$^d$, —(SO)OR$^d$, —SO$_3$R$^d$, —CONR$^e{}_2$, —O(CO)NR$^e{}_2$, —NR$^f$(CO)NR$^e{}_2$, —NR$^f$(CO)OR$^d$, —NR$^f$COR$^d$, —(SO$_2$)NR$^e{}_2$, —NR$^f$SO$_2$R$^d$, —(CH$_2$)$_s$NR$^d{}_2$, or optionally substituted aryl, aralkyl or C1-C5 alkyl. In the preceding, s is from 0 to 5, each R$^d$ and R$^f$ are, independently, —H, aryl, aralkyl, C1-C5 alkyl, or C1-C5 haloalkyl, and each R$^e$ are, independently, —H, aryl, aralkyl, or C1-C5 alkyl, and NR$^e{}_2$ is a nonaromatic heterocyclic group, for example, piperidinyl, morpholinyl, and the like. More preferably, R1 is halogen, —CN, —NO$_2$, —CF$_3$—OCF$_3$, —OR$^d$, —(CO)R$^d$, —(CO)OR$^d$, —O(CO)R$^d$, —CONR$^e{}_2$, —O(CO)NR$^e{}_2$, —NR$^f$(CO)OR$^d$, —NR$^f$COR$^d$, —(SO$_2$)NR$^e{}_2$, —NR$^f$SO$_2$R$^d$, —(CH$_2$)$_s$NR$^d{}_2$, or optionally substituted aryl, aralkyl or C1-C5 alkyl. Even more preferably, R1 is —H, —OH, —F, —CH$_3$, —CF$_3$, —OCH$_3$ or —OCF$_3$. Most preferably, R1 is —H.

In one embodiment, R3 in structural Formula I is an optionally substituted phenyl, pyridyl, benzo[1,3]dioxolyl, 2,3-dihydro-benzo[1,4]dioxinyl, pyrimidyl, pyrazyl, furanyl, pyrrolyl, thienyl, oxazolyl, isooxazolyl, thiazolyl, isothiazolyl, imidazolyl naphthyl, quinolinyl, biphenyl, benzopyrimidyl, benzopyrazyl, benzofuranyl, indolyl, benzothienyl, benzoxazolyl, benzoisooxazolyl, benzothiazolyl, benzoisothiazolyl, or benzimidazolyl group. Suitable optional substituents for the group represented by R3 are provided herein below.

More preferably, R3 in structural Formula I is represented by one of structural formulas R3-i to R3-v:

R3-i

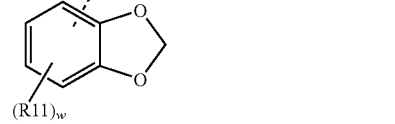

R3-ii

R3-iii

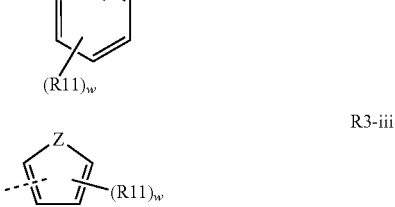

R3-iv

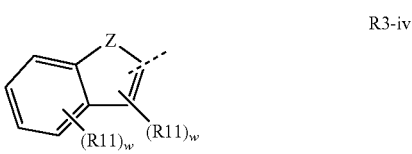

R3-v

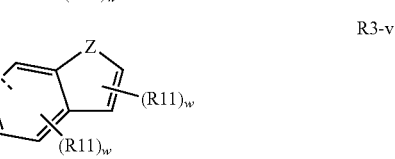

In structural formulas R3-i to R3-v, Y is —N—, —CH—, or —CR11-; Z is —NR$^z$—, —S—, or —O—, wherein R$^z$ is —H or C1-C3 alkyl, more preferably —H or methyl, or most preferably —H; the variable w is 0, 1, 2, or 3; each R11 are, independently, halogen, —CN, —NO$_2$, —CF$_3$, —OCF$_3$, —OR$^1$, —(CO)R$^1$, —(CO)OR$^1$, —O(CO)R$^1$, —(CO)O(CO)R$^1$, —(CS)OR$^1$, —(SO)OR$^1$, —SO$_3$R$^1$, —CONR$^m{}_2$, —O(CO)NR$^m{}_2$, —NR$''$(CO)NR$^m{}_2$, —NR$''$(CO)OR$^1$, —NR$''$COR$^1$, —(SO$_2$)NR$^m{}_2$)—NR$''$SO$_2$R$^1$, —(CH$_2$)$_u$NR$^1{}_2$, or optionally substituted aryl, aralkyl, or C1-C5 alkyl. In the preceding, u is 0 to 5, each R$^1$ and R$''$ are, independently, —H, aryl, or aralkyl, C1-C5 alkyl, or C1-C5 haloalkyl, and each R$^m$ is independently —H, aryl, aralkyl, or C1-C5 alkyl, or NR$^m{}_2$ is a nonaromatic heterocyclic group.

Even more preferably, R3 in structural Formula I is represented by one of structural formulas R3-i' to R3-v':

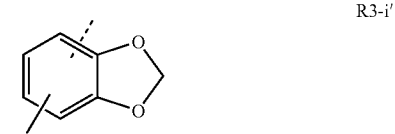

R3-i'

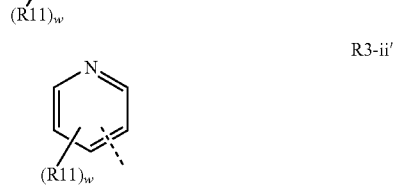

R3-ii'

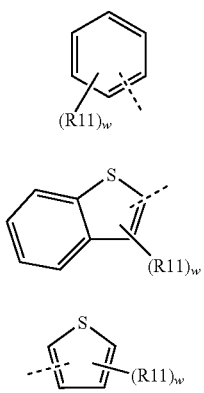
In structural formulas R3-i' to R3-v', w is 0, 1, 2, or 3, and each $R^{11}$ is independently —OH, —$NO_2$, —F, —Cl, —Br, C1-C4 alkyl, C1-C4 alkoxy, —$CF_3$, or —$OCF_3$.
Still more preferably, R3 is represented by one of structural formulas $R3^a$ to $R3^r$:
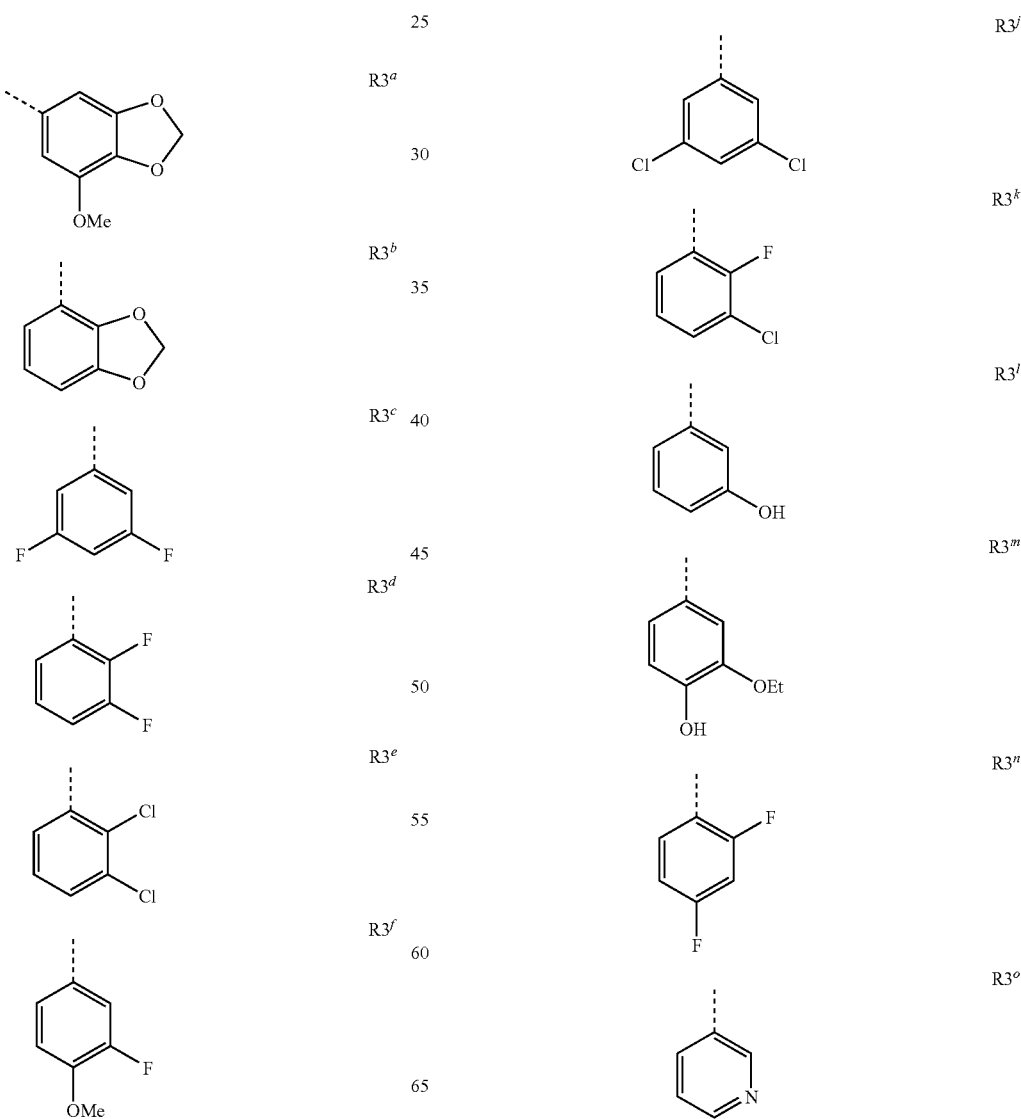

-continued

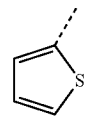
R3$^p$

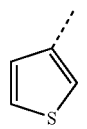
R3$^q$

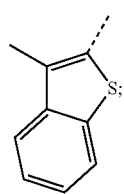
R3$^r$

Most preferably, R3 is represented by structural formula R3$^d$, R3$^e$, or R3$^f$.

R4 in structural Formula I is optionally further substituted as described below in the section describing suitable substituents for aryl, heteroaryl, aliphatic, and cycloalkyl groups. More preferably, R4 is a substituted phenyl, pyridyl, pyrimidyl, pyrazyl, naphthyl, biphenyl, phenyl-pyridyl, quinolinyl, benzopyrimidyl, benzopyrazyl, cyclopropyl, cyclobutyl, cyclopentyl, cyclopentenyl, cyclohexyl, cyclohexenyl, or a C2-C8 alkenyl group.

More preferably, R4 is represented by one of structural formulas R4-i to R4-vii:

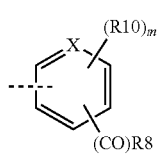
R4-i

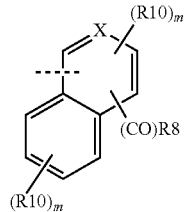
R4-ii

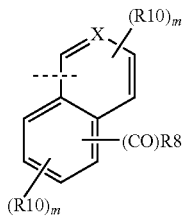
R4-iii

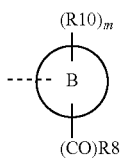
R4-iii

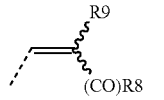
R4-iv

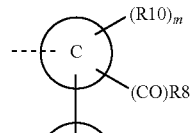
R4-v

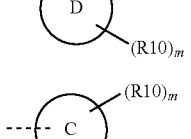
R4-vii

In structural formulas R4-i to R4-vii, each m is independently 0, 1, 2, or 3, and X is —N—, —CH—, or —CR10-; Ring B is C3-C6 cycloalkyl or C3-C6 cycloalkenyl; Rings C and D are each independently aryl or heteroaryl; R8 is —OR$^q$ or —NR$^r_2$; R9 is —H, aryl, aralkyl, or C1-C6 aliphatic; each R10 is independently halogen, —CN, —NO$_2$, —CF$_3$, —OCF$_3$, —OR$^i$, —(CO)R$^i$, —(CO)OR$^i$, —O(CO)R$^i$, —(CO)O(CO)R$^i$, —(CS)R$^i$, —(SO)OR$^i$, —SO$_3$R$^i$, —CONR$^j_2$, —O(CO)NR$^j_2$, —NR$^k$(CO)NR$^j_2$, —NR$^k$(CO)OR$^i$, —NR$^k$COR$^i$, —(SO$_2$)NR$^j_2$, —NR$^k$SO$_2$R$^i$, —(CH$_2$)$_t$NR$^j_2$, or optionally substituted aryl, aralkyl or C1-C5 alkyl; the variable t is 0 to 5 and each R$^i$ and R$^k$ is independently —H, aryl, aralkyl, C1-C5 alkyl, or C1-C5 haloalkyl; each R$^j$ and R$^r$ is independently —H, aryl, aralkyl, or C1-C5 alkyl, or each NR$^j_2$ and NR$^r_2$ are, independently, a nonaromatic heterocyclic group; and R$^q$ is —H or optionally substituted aryl, aroyl, aralkyl, aralkanoyl, C1-C5 alkyl, or C1-C5 alkanoyl.

Even more preferably, R4 is represented by one of structural formulas R4-i' to R4-vii':

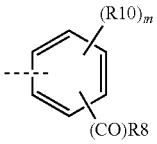
R4-i'

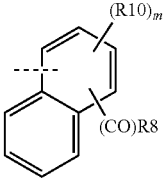
R4-ii'

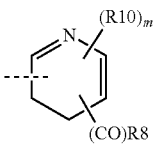
R4-iii'

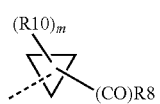
R4-iv′

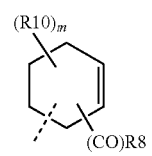
R4-v′

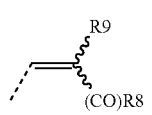
R4-vi′

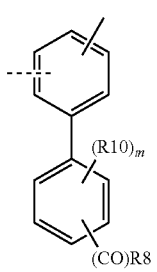
R4-vii′

In structural formulas R4-i′ to R4-vii′, each m is independently 0, 1, 2, or 3; R8 is —OH, C1-C5 alkoxy, or C1-C5 alkanoyloxy; R9 is —H or C1-C6 aliphatic; and each R10 is independently —OH, —NO$_2$, —F, —Cl, —Br, C1-C4 alkyl, C1-C4 alkoxy, —CF$_3$, or —OCF$_3$.

Still more preferably, R4 is represented by one of structural formulas R4$^a$ to R4$^q$:

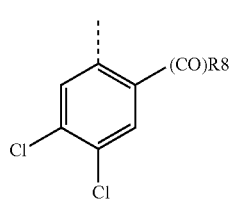
R4$^a$

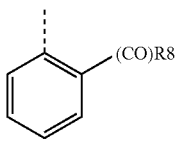
R4$^b$

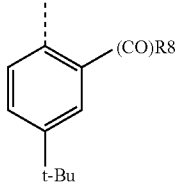
R4$^c$

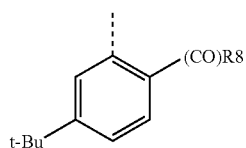
R4$^d$

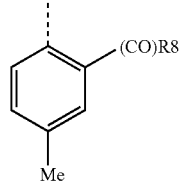
R4$^e$

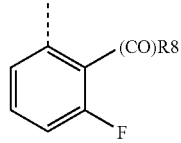
R4$^f$

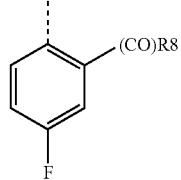
R4$^g$

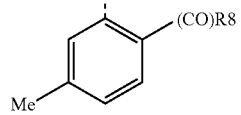
R4$^h$

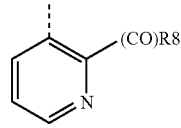
R4$^i$

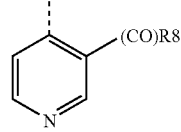
R4$^j$

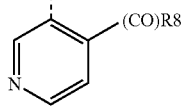
R4$^k$

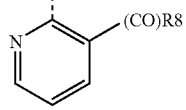
R4$^l$

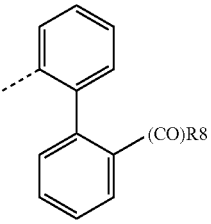
R4$^m$

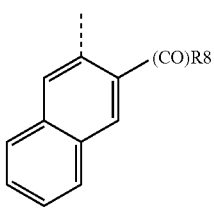
R4ⁿ

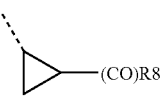
R4ᵒ

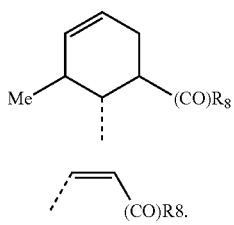
R4ᵖ

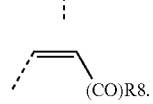
R4ᵠ

Most preferably, R4 is represented by structural formula R4$^a$, R4$^c$, or R4$^e$. In preferred embodiments of R4$^a$ to R4$^q$, R8 is —NR$^y_2$, —OH, C1-C5 alkoxy, or C1-C5 alkanoyloxy, wherein each R$^y$ is independently —H or C1-C3 alkyl. Even more preferably, R8 is —OH or C1-C4 alkoxy, or still more preferably, —OH, —OCH$_3$, or —OCH$_2$CH$_3$. Most preferably, R8 is OCH$_3$ or —OCH$_2$CH$_3$.

In preferred embodiments, of R4$^a$ to R4$^q$, R8 is —OH, OCH$_3$ or —OCH$_2$CH$_3$.

In structural Formula I, R3 is represented by one of structural formulas R3-i to R3-v or R4 is represented by one of structural formulas R4-i to R4-vii. More preferably, R3 is represented by one of structural formulas R3-i to R3-v and R4 is represented by one of structural formulas R4-i to R4-vii. In still another embodiment, in structural Formula I, R3 is represented by one of structural formulas R3-i' to R3-v' or R4 is represented by one of structural formulas R4-i' to R4-vi'. More preferably, R3 is represented by one of structural formulas R3-i' to R3-v' and R4 is represented by one of structural formulas R4-i' to R4-vi'. In another preferred embodiment, for structural Formula I, R3 is represented by one of structural formulas R3$^a$ to R3$^r$, or R4 is represented by one of structural formulas R4$^a$ to R4. Preferably, R3 is represented by one of structural formulas R3$^a$ to R3$^r$, and R4 is represented by one of structural formulas R4$^a$ to R4. More preferably, R3 is represented by structural formula R3$^d$, R3$^e$, or R3$^f$, or R4 is represented by structural formula R4$^a$, R4$^c$, or R4$^e$. Even more preferably, R3 is represented by structural formula R3$^d$, R3$^e$, or R3$^f$, and R4 is represented by structural formula R4$^a$, R4$^c$, or R4$^e$.

In another embodiment of Formula I, ring A is an imidazole or thiophene moiety that is optionally substituted one or more times with C1-C4 alkyl; R3 is phenyl optionally substituted one or more times with halogen; L is (CO); R4 is phenyl optionally independently substituted one or more times with halogen or CO$_2$H; and R5 is H or CO$_2$H.

In an exemplary embodiment, the compound of formula I is of the formula 5:

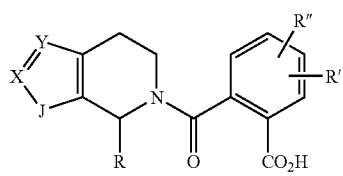

5 wherein R' and R" are each independently hydrogen, halogen, alkyl or alkoxy.

In one embodiment, of Formula 5, Y is N or CH or C, J is NH, O or S and X is CH.

In another exemplary embodiment, the compound of formula I is of the formula 6:

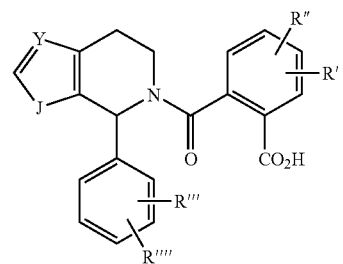

6 wherein R' and R" are each, independently, hydrogen, alkyl or halogen; R''' and R'''' are each, independently, hydrogen, alkoxy or halogen; and Y and J are each, independently, S or N.

In other embodiments, the compound, the compound of the method, and the compound of the pharmaceutical composition are each represented by individual compounds provided in Table 1.

TABLE 1

| Compound 1 | 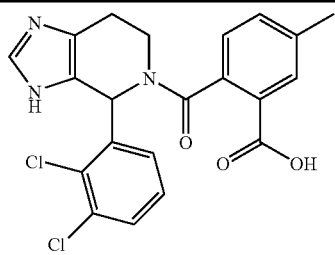 |
|---|---|
| Compound 2 | 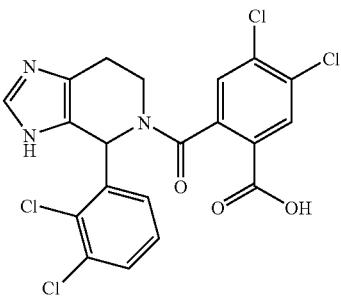 |

TABLE 1-continued
Compound 3
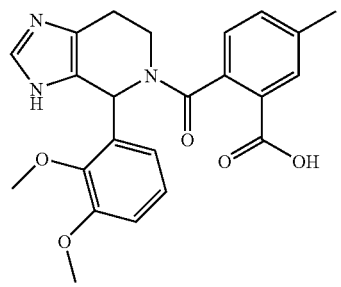
Compound 4
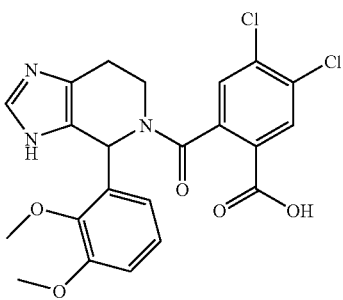
Compound 5
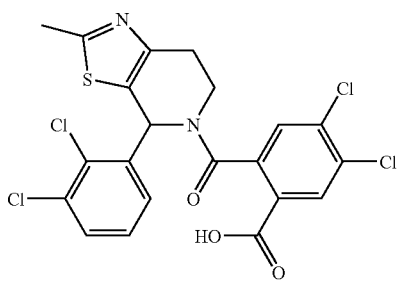
Compound 6
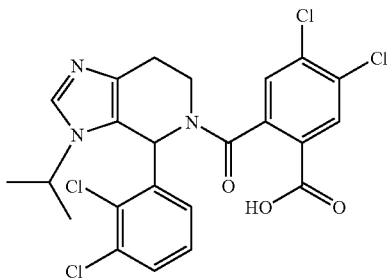
Compound 7
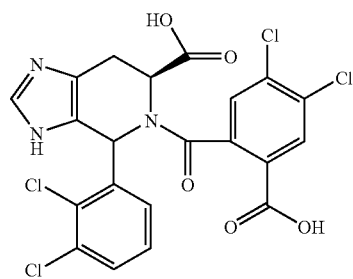
TABLE 1-continued
Compound 8
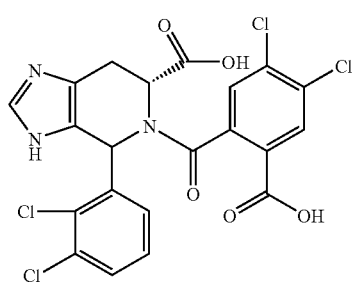
Compound 9
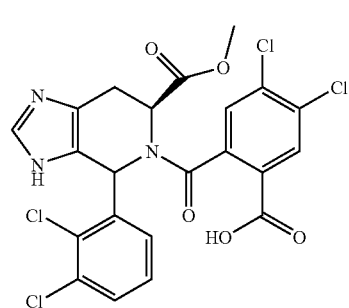
Compound 10
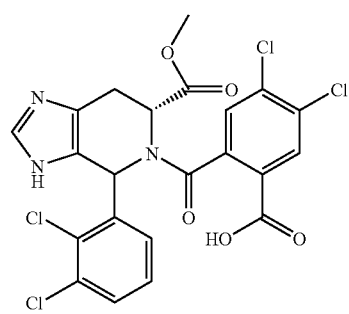
Compound 11
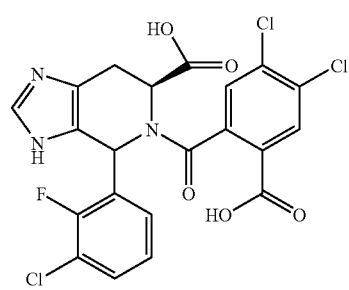
Compound 12
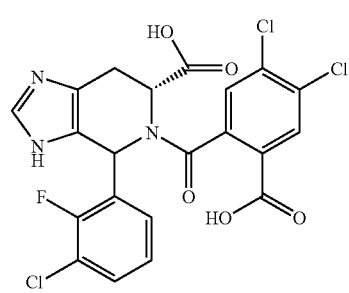

TABLE 1-continued

Compound 13

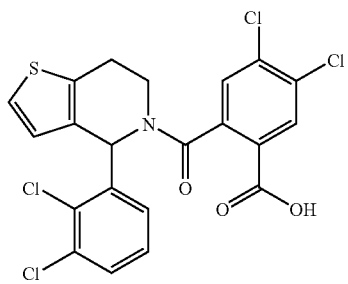

Compound 14

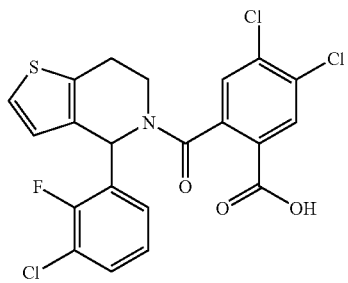

Compound 15

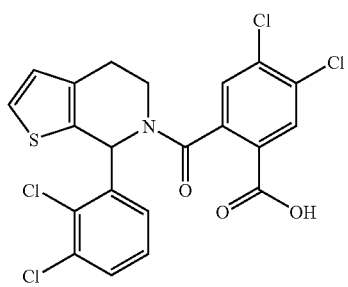

Compound 16

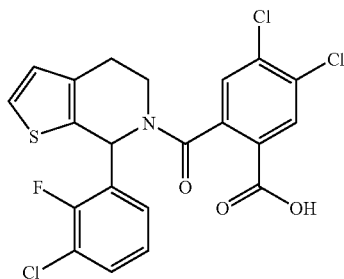

In a particular embodiment, the compounds of Table 1 can be used to treat a bacterial infection in a subject in need thereof.

Compounds of the invention may be useful in the treatment of bacterial infections dependent on PPAT. Thus, as a further embodiment, the present invention provides the use of a compound of formula I-a in therapy. In a further embodiment, the therapy is selected from a disease which is ameliorated by inhibition of PPAT.

A "subject" includes mammals, e.g., humans, companion animals (e.g., dogs, cats, birds, aquarium fish, reptiles, and the like), farm animals (e.g., cows, sheep, pigs, horses, fowl, farm-raised fish and the like) and laboratory animals (e.g., rats, mice, guinea pigs, birds, aquarium fish, reptiles, and the like). Alternatively, the subject is a warm-blooded animal. More preferably, the subject is a mammal. Most preferably, the subject is human.

A subject in need of treatment has a bacterial infection (or has been exposed to an infectious environment where bacteria are present, e.g., in a hospital) the symptoms of which may be alleviated by administering an effective amount of the disclosed bicyclic derivatives. For example, a subject in need of treatment can have an infection for which the disclosed bicyclic derivatives can be administered as a treatment. In another example, a subject in need of treatment can have an open wound or burn injury, or can have a compromised immune system, for which the disclosed PPAT inhibitors can be administered as a prophylactic. Thus, a subject can be treated therapeutically or prophylactically. More preferably, a subject is treated therapeutically.

Typically, the subject is treated for a bacterial infection caused by a bacteria of a genus selected from *Allochromatium, Acinetobacter, Bacillus, Campylobacter, Chlamydia, Chlamydophila, Clostridium, Citrobacter, Escherichia, Enterobacter, Enterococcus, Francisella, Haemophilus, Helicobacter, Klebsiella, Listeria, Moraxella, Mycobacterium, Neisseria, Proteus, Pseudomonas, Salmonella, erratia, Shigella, Stenotrophomonas, Staphyloccocus, Streptococcus, Synechococcus, Vibrio*, and *Yersina*.

More preferably, the subject is treated for a bacterial infection from *Allochromatium vinosum, Acinetobacter baumanii, Bacillus anthracis, Campylobacter jejuni, Chlamydia trachomatis, Chlamydia pneumoniae, Clostridium* spp., *Citrobacter* spp., *Escherichia coli, Enterobacter* spp., *Enterococcus faecalis., Enterococcus faecium, Francisella tularensis, Haemophilus influenzas, Helicobacter pylori, Klebsiella* spp., *Listeria moiwcytogenes, Moraxella catarrhalis, Mycobacterium tuberculosis, Neisseria meningitidis, Neisseria gonorrhoeae, Proteus mirabilis, Proteus vulgaris, Pseudomonas aeruginosa, Salmonella* spp., *Serratia* spp., *Shigella* spp., *Stenotrophomonas maltophilia, Staphyloccocus aureus, Staphyloccocus epidermidis, Streptococcus pneumoniae, Streptococcus pyogenes, Streptococcus agalactiae, Yersinapestis*, and *Yersina enterocolitica*, and the like.

Preferably, the subject is treated for a bacterial infection caused by a bacterium that expresses a PPAT protein. As used herein, a PPAT protein is a phosphopantetheine adenylransferase enzyme, i.e., systematic name ATP:pantetheine-4'-phosphate adenylyltransferase, IUBMB systematic classification EC 2.7.7.3, (see International Union of Biochemistry and Molecular Biology, www.chem.qmul.ac.uk/iubmb/).

In one embodiment, a subject is also concurrently treated for a fungal infection, for example, a fungal infection caused by a pathogenic dermatophyte, e.g., a species of the genera *Trichophyton, Tinea, Microspormn, Epidermophyton* and the like; or a pathogenic filamentous fungus, e.g., a species of genera such as *Aspergillus, Histoplasma, Cryptococcus, Microspormn*, and the like; or a pathogenic non-filamentous fungus, e.g., a yeast, for example, a species of the genera *Candida, Malassezia, Trichosporon, Rhodotorula, Torulopsis, Blastomyces, Paracoccidioides, Coccidioides*, and the like. Preferably, the subject is concurrently treated for a fungal infection resulting from a species of the genera *Aspergillus* or *Trichophyton*. Species of *Trichophyton* include, for example, *T. mentagrophytes, T. rubrum, T. schoenleinii, T. tonsurans, T. verrucosum*, and *T. violaceum*. Species of *Aspergillus* include, for example, *A. fumigatus, A. flavus, A. niger, A. amstelodami, A. candidus, A. carneus, A. nidulans, A oryzae, A. restrictus, A. sydowi, A. terreus, A. ustus, A. versicolor, A. caesiellus, A. clavatus, A. avenaceus*, and *A. deflectus*. More preferably, the subject is concurrently treated therapeutically for a fungal infection caused by a species of the genus *Aspergillus* selected from *A. fumigatus, A. flavits, A. niger, A. canstelodami, A. candidus, A. carneus, A. nidulans, A oryzae, A. restrictus, A. sydowi, A. terreus, A. ustus, A. versicolor, A. caesiellus, A. clavatus, A. avenaceus*, and. *A.*

*deflectus*. Even more preferably the subject is concurrently treated therapeutically for a fungal infection caused by *Aspergillus fumigatus* or *A spergillus niger*, and most preferably, *Aspergillus fumigatus*.

An "effective amount" of a compound of the disclosed invention is the quantity that, when administered to a subject in need of treatment, improves the prognosis of the subject, e.g., delays the onset of and/or reduces the severity of one or more of the subject's symptoms associated with a bacterial infection. The amount of the disclosed compound to be administered to a subject will depend on the particular disease, the mode of administration, co-administered compounds, if any, and the characteristics of the subject, such as general health, other diseases, age, sex, genotype, body weight and tolerance to drugs. The skilled artisan will be able to determine appropriate dosages depending on these and other factors. Effective amounts of the disclosed compounds typically range between about 0.01 mg/kg per day and about 100 mg/kg per day, and preferably between 0.1 mg/kg per day and about 10 mg/kg/day. Techniques for administration of the disclosed compounds of the invention can be found in *Remington: the Science and Practice of Pharmacy,* $19^{th}$ edition, Mack Publishing Co., Easton, Pa. (1995), the entire teachings of which are incorporated herein by reference.

A "pharmaceutically acceptable salt" of the disclosed compound is a product of the disclosed compound that contains an ionic bond, and is typically produced by reacting the disclosed compound with either an acid or a base, suitable for administering to a subject.

For example, an acid salt of a compound containing an amine or other basic group can be obtained by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures), succinates, benzoates and salts with amino acids such as glutamic acid.

Salts of compounds containing a carboxylic acid or other acidic functional groups can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-3-phenethylamine, dehydroabietylamine, N,N'-bisdehydroabietylamine, glucamine, N-methylglucamine, collidine, quinine, quinoline, and basic amino acid such as lysine and arginine.

Certain compounds and their salts may also exist in the form of solvates, for example hydrates, and the present invention includes each solvate and mixtures thereof.

As used herein, a "pharmaceutical composition" is a formulation containing the disclosed compounds in a form suitable for administration to a subject. The pharmaceutical composition can be in bulk or in unit dosage form. The unit dosage form can be in any of a variety of forms, including, for example, a capsule, an IV bag, a tablet, a single pump on an aerosol inhaler, or a vial. The quantity of active ingredient (i.e., a formulation of the disclosed compound or salts thereof) in a unit dose of composition is an effective amount and may be varied according to the particular treatment involved. It is appreciated that it may be necessary to make routine variations to the dosage depending on the age and condition of the patient. The dosage will also depend on the route of administration. A variety of routes are contemplated, including topical, oral, pulmonary, rectal, vaginal, parenteral, transdermal, subcutaneous, intravenous, intramuscular, intraperitoneal and intranasal.

The compounds described herein, and the pharmaceutically acceptable salts thereof, can be used in pharmaceutical preparations in combination with a pharmaceutically acceptable carrier or diluent. Suitable pharmaceutically acceptable carriers include inert solid fillers or diluents and sterile aqueous or organic solutions.

The compounds will be present in such pharmaceutical compositions in amounts sufficient to provide the desired dosage amount in the range described herein. Techniques for formulation and administration of the disclosed compounds of the Invention can be found in *Remington: the Science and Practice of Pharmacy*, above.

For oral administration, the disclosed compounds or salts thereof can be combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch or alginic acid; a lubricant such as magnesium stearate; and/or a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor, and the like.

For parental administration of the disclosed compounds, or salts, solvates, or hydrates thereof, can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition to the formulations previously described, the compounds may also be formulated as a depot preparation. Suitable formulations of this type include biocompatible and biodegradable polymeric hydrogel formulations using crosslinked or water insoluble polysaccharide formulations, polymerizable polyethylene oxide formulations, impregnated membranes, and the like. Such long acting formulations may be administered by implantation or transcutaneous delivery (for example subcutaneously or intramuscularly), intramuscular injection or a transdermal patch. Preferably, they are implanted in, or applied to, the microenvironment of an affected organ or tissue, for example, a membrane impregnated with the disclosed compound can be applied to an open wound or burn injury. Thus, for example, the compounds may be formulated with suitable polymeric or hydrophobic materials, for example, as an emulsion in acceptable oil, or ion exchange resins, or as sparingly soluble derivatives, for example, as a sparingly soluble salt.

For topical administration, suitable formulations may include biocompatible oil, wax, gel, powder, polymer, or other liquid or solid carriers. Such formulations may be administered by applying directly to affected tissues, for example, a liquid formulation to treat infection of conjunctival tissue can be administered dropwise to the subject's eye, a cream formulation can be administer to a wound site, or a bandage may be impregnated with a formulation, and the like.

For rectal administration, suitable pharmaceutical compositions are, for example, topical preparations, suppositories or enemas.

For vaginal administration, suitable pharmaceutical compositions are, for example, topical preparations, pessaries, tampons, creams, gels, pastes, foams or sprays.

In addition, the compounds may also be formulated to deliver the active agent by pulmonary administration, e.g., administration of an aerosol formulation containing the active agent from, for example, a manual pump spray, nebulizer or pressurized metered-dose inhaler. Suitable formulations of this type can also include other agents, such as antistatic agents, to maintain the disclosed compounds as effective aerosols.

The term "pulmonary" as used herein refers to any part, tissue or organ whose primary function is gas exchange with the external environment, i.e., $O_2/CO_2$ exchange, within a patient. "Pulmonary" typically refers to the tissues of the respiratory tract. Thus, the phrase "pulmonary administration" refers to administering the formulations described herein to any part, tissue or organ whose primary function is gas exchange with the external environment (e.g., mouth, nose, pharynx, oropharynx, laryngopharynx, larynx, trachea, carina, bronchi, bronchioles, alveoli). For purposes of the present invention, "pulmonary" is also meant to include a tissue or cavity that is contingent to the respiratory tract, in particular, the sinuses.

A drug delivery device for delivering aerosols comprises a suitable aerosol canister with a metering valve containing a pharmaceutical aerosol formulation as described and an actuator housing adapted to hold the canister and allow for drug delivery. The canister in the drug delivery device has a head space representing greater than about 15% of the total volume of the canister. Often, the polymer intended for pulmonary administration is dissolved, suspended or emulsified in a mixture of a solvent, surfactant and propellant. The mixture is maintained under pressure in a canister that has been sealed with a metering valve.

For nasal administration, either a solid or a liquid carrier can be used. The solid carrier includes a coarse powder having particle size in the range of, for example, from about 20 to about 500 microns and such formulation is administered by rapid inhalation through the nasal passages. Where the liquid carrier is used, the formulation may be administered as a nasal spray or drops and may include oil or aqueous solutions of the active ingredients.

In addition to the formulations described above, a formulation can optionally include, or be co-administered with one or more additional drugs, e.g., other antibiotics, anti-inflammatories, antirungals, antivirals, immunomodulators, antiprotozoals, steroids, decongestants, bronchodilators, and the like. For example, the disclosed compound can be co-administered with drugs such as such as ibuprofen, prednisone (corticosteroid) pentoxifylline, Amphotericin B, Fluconazole, Ketoconazol, Itraconazol, penicillin, ampicillin, amoxicillin, and the like. The formulation may also contain preserving agents, solubilizing agents, chemical buffers, surfactants, emulsifiers, colorants, odorants and sweeteners.

The term "derivative," e.g., in the term "bicyclic derivatives," refers to compounds that have a common core structure, and are substituted with various groups as described herein. For example, all of the compounds represented by structural Formula I are bicyclic derivatives, and have structural Formula I as a common core.

In the structural formulas depicted herein, a dashed line indicates a bond by which the depicted or moiety or group is connected to the remainder of the molecule. For example, the dashed line in R4-i indicates the bond that connects the depicted group to another structural formula. A dashed or solid line across a bond in a ring, for example, the solid line from R11 in R4-i, indicates that the represented bond can be connected to any substitutable atom in the ring. A zig-zag line indicates either cis or trans arrangement of the respective substituents with respect to the bond represented by the dashed line.

The term "aryl" group refers to carbocyclic aromatic groups such as phenyl, naphthyl, and anthracyl. The term "heteroaryl" group refers to heteroaromatic groups such as imidazolyl, isoimidazolyl, thienyl, furanyl, pyridyl, pyrimidyl, pyranyl, pyrazolyl, pyrrolyl, pyrazinyl, thiazolyl, isothiazolyl, oxazolyl, isooxazolyl, 1,2,3-triazolyl, 1,2,4-triazolyl, and tetrazolyl. As used herein, a "heteroaryl" group is a 5 membered carbocyclic ring containing at least one N, S, or O atom and two double bonds, or a 6 membered carbocyclic ring containing at least one N, S, or O atom and three double bonds.

The term "nonaromatic heterocyclic" refers to non-aromatic ring systems typically having four to eight members, preferably five to six, in which one or more ring carbons, preferably one to four, are each replaced by a heteroatom such as N, O, or S. Examples of non-aromatic heterocyclic rings include 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-raorpholinyl, 2-thiomorpholinyl, 3-thiomorpholinyl, 4-thiomorpholinyl, 1-pyrrolidinyl, 2-pyrrolidinyl, 3-pyrorolidinyl, 1-piperazinyl, 2-piperazinyl, 1-piperidinyl, 2-piperidinyl, 3-piperidinyl, 4-piperidinyl, 4-thiazolidinyl, 5 diazolonyl, N-substituted diazolonyl, and 1-pthalimidinyl.

The disclosed compounds can contain one or more chiral centers. The presence of chiral centers in a molecule gives rise to stereoisomers. For example, a pair of optical isomers, referred to as "enantiomers", exist for every chiral center in a molecule. A pair of diastereomers exists for every chiral center in a compound having two or more chiral centers. Where the structural formulas do not explicitly depict stereochemistry, for example in structural Formula I, it is to be understood that these formulas encompass enantiomers free from the corresponding optical isomer, racemic mixtures, mixtures enriched in one enantiomer relative to its corresponding optical isomer, a diastereomer free of other diastereomers, a pair of diastereomers free from other diastereomeric pairs, mixtures of diasteromers, mixtures of diasteromeric pairs, mixtures of diasteromers in which one diastereomer is enriched relative to the other diastereomer(s) and mixtures of diasteromeric pairs in which one diastereomeric pair is enriched relative to the other diastereomeric pair(s).

The term "alkyl" used alone or as part of a larger moiety (e.g., aralkyl, alkoxy, alkylamino, alkylaminocarbonyl, haloalkyl), is a straight or branched non-aromatic hydrocarbon which is completely saturated. Typically, a straight or branched alkyl group has from 1 to about 10 carbon atoms, preferably from 1 to about 5 if not otherwise specified. Examples of suitable straight or branched alkyl groups include methyl, ethyl, n-propyl, 2-propyl, w-butyl, sec-butyl, tert-butyl, pentyl, hexyl, heptyl or octyl. A C1-C10 straight or branched alkyl group or a C3-C8 cyclic alkyl group can also be referred to as a "lower alkyl" group. An "alkoxy" group refers to an alkyl group that is connected through an intervening oxygen atom, e.g., methoxy, ethoxy, 2-propyloxy, tert-butoxy, 2-butyloxy, 3-pentyloxy, and the like.

The terms "optionally halogenated alkyl", and "optionally halogenated alkoxy", as used herein, includes the respective group substituted with one or more of —F, —Cl, —Br, or —I.

The terms "alkanoyl", "aroyl", and the like, as used herein, indicates the respective group connected through an intervening carbonyl, for example, —(CO)CH$_2$CH$_3$, benzoyl, and the like. The terms "alkanoyloxy", "aroyloxy", and the like, as used herein, indicates the respective group connected through an intervening carboxylate, for example, —O(CO)CH$_2$CH$_3$, —O(CO)C$_6$H$_5$, and the like.

The term "cycloalkyl group" is a cyclic alkyl group has from 3 to about 10 carbon atoms, preferably from 3 to about 7. Examples of suitable cycloalkyl groups include cyclopropyl, cyclobutyl, cyclopentyl, cyclohexyl, cycloheptyl and cyclooctyl.

A "cycloalkoxy" group refers to a cycloalkyl group that is connected through an intervening oxygen atom, e.g., cyclopentyloxy, cyclohexyloxy, and the like.

The term "aliphatic" includes branched and linear alkyl groups that contain one or more units of carbon-carbon unsaturation, i.e., carbon-carbon double or triple bonds. A cycloaliphatic group is a cyclic aliphatic group, for example, cyclohexenyl or cyclopentenyl.

The terms "aralkyl," "heteroaralkyl," "cycloalkylalkyl," "cycloaliphaticalkyl," and "nonaromatic heterocycloalkyl" refer to aryl, heteroaryl, cycloalkyl, cycloaliphatic, and non-aromatic heterocyclic groups, respectively, that are connected through an alkyl chain, e.g., benzyl, —CH$_2$CH$_2$-pyridine, (3-cyclohexyl)propyl, and the like.

The terms biaryl, biheteroaryl, aryl-heteroaryl and heteroaryl-aryl, as used herein, indicate two aryl groups connected by a single covalent bond, two heteroaryl groups connected by a single covalent bond, an aryl and heteroaryl group connected by single covalent bond, and a heteroaryl and aryl group connected by a single covalent bond, respectively. Examples of biaryl, biheteroaryl, heteroaryl-aryl and aryl-heteroaryl groups include biphenyl, bipyridyl, pyrimidyl-phenyl, and phenyl-pyridyl, respectively. When a biaryl, biheteroaryl, heteroaryl-aryl or aryl-heteroaryl group is a substituent, as in the definition of R4 for structural Formula I, the first recited group is bonded to the remainder of the molecule, i.e., "L" in structural Formula I. For example, when R4 in structural Formula I is a phenyl-pyridyl group, the phenyl of the phenyl-pyridyl group is bonded to L.

An "acyclic" group is a substituent that does not contain a ring. A "monocyclic" group contains only a single ring, for example, a phenyl ring that is not fused to another ring. A "polycyclic" group is a group that contains multiple fused rings, for example, naphthyl.

A "substitutable atom" is any atom such as nitrogen or carbon that is bonded through a single covalent bond to a hydrogen atom, wherein the hydrogen atom can be replaced with another group. A "substitutable ring atom" in an aromatic ring is any ring atom, e.g., a carbon or nitrogen, which is bonded by a single covalent bond to a hydrogen atom, wherein the hydrogen atom can be replaced with another group.

Suitable substituents are those that do not substantially interfere with the pharmaceutical activity of the disclosed compound. A compound or group can have one or more substituents, which can be identical or different. Examples of suitable substituents for a substitutable carbon atom in an alkyl, aliphatic, cycloalkyl, cycloaliphatic, non-aromatic heterocyclic, aryl, or heteroaryl group include —OH, halogen (—Br, —Cl, —I and —F), —R, —OR, —CH$_2$R, —CH$_2$CH$_2$R, —OCH$_2$R, —CH$_2$OR, —CH$_2$CH$_2$OR, —CH$_2$OC(O)R, —O—COR, —COR, —SR, —SCH$_2$R, —CH$_2$SR, —SOR, —SO$_2$R, —CN, —NO$_2$, —COOH, —SO$_3$H, —NH$_2$, —NHR, —N(R)$_2$, —COOR, —CH$_2$COOR, —CH$_2$CH$_2$COOR, —CHO, —CONH$_2$, —CONHR, —CON(R)$_2$, —NHCOR, —NRCOR, —NHCONH$_2$, —NHCONRH, —NHCON(R)$_2$, —NRCONH$_2$, —NRCONRH, —NRCON(R)$_2$, —C(=NH)—NH$_2$, —C(=NH)—NHR, —C(=NH)—N(R)$_2$, —C(=NR)—NH$_2$, —C(=NR)—NHR, —C(=NR)—N(R)$_2$, —NH—C(=NH)—NH$_2$, —NH—C(=NH)—NHR, —NH—C(=NH)—N(R)$_2$, —NH—C(=NR)—NH$_2$, —NH—C(=NR)—NHR, —NH—C(=NR)—N(R)$_2$, —NRH—C(=NH)—NH$_2$, —NR—C(=NH)—NHR, —NR—C(=NH)—N(R)$_2$, —NR—C(=NR)—NH$_2$, —NR—C(=NR)—NHR, —NR—C(=NR)—N(R)$_2$, —SO$_2$NH$_2$, —SO$_2$NHR, —SO$_2$NR$_2$, —SH, —SO$_k$R (k is 0, 1 or 2) and —NH—C(=NH)—NH$_2$. Each R is independently an alkyl, cycloalkyl, benzyl, aromatic, heteroaromatic, or N-anilinyl group that is optionally substituted. Preferably, R is unsubstituted. In addition, —N(R)$_2$, taken together, can also form a substituted or unsubstituted heterocyclic group, such as pyrrolidinyl, piperidinyl, morpholinyl and thiomorpholinyl. Examples of substituents on group represented by R include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

Suitable substituents on the nitrogen of a heterocyclic group or heteroaromatic group include —R', —N(R')$_2$, —C(O)R', —CO$_2$R, —C(O)C(O)R', —C(O)CH$_2$ C(O)R', —SO$_2$R', —SO$_2$N(R')$_2$, —C(=S)N(R')$_2$, —C(=NH)—N (R')$_2$, and —NR'SO$_2$R', wherein R' is hydrogen, an alkyl, alkoxy, cycloalkyl, cycloalkoxy, phenyl, phenoxy, benzyl, benzyloxy, heteroaromatic, or heterocyclic group that is optionally substituted. Examples of substituents on the groups represented by R' include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl. Preferably, R' is unsubstituted.

Advantageously, the present invention also provides kits for use by a consumer for treating disease. The kits comprise a) a pharmaceutical composition comprising an antibiotic and a pharmaceutically acceptable carrier, vehicle or diluent; and, optionally, b) instructions describing a method of using the pharmaceutical composition for treating the specific disease. The instructions may also indicate that the kit is for treating disease while substantially reducing the concomitant liability of adverse effects associated with antibiotic administration.

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," ... etc. ... "Second Week, Monday, Tuesday, ..." etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

EXEMPLIFICATION

Example 1

Synthesis of PPAT Inhibitors of Structural Formula I

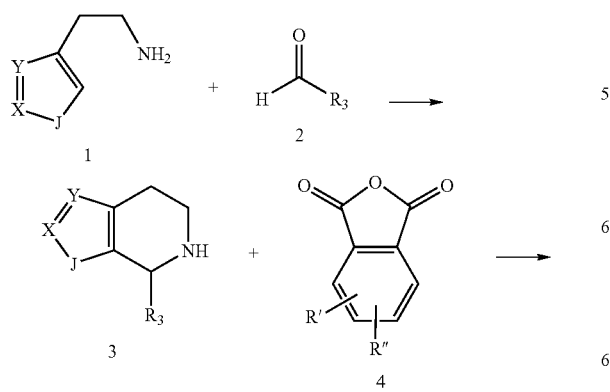

-continued

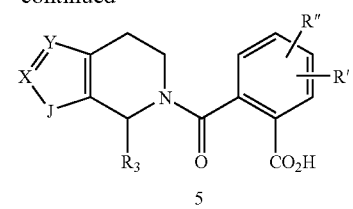

5

R' and R" are each independently H, halogen or alkoxy

A mixture of amine bis-hydrochloride 1, anhydrous sodium acetate and aldehyde 2 in pyridine is heated to reflux under $N_2$ for 16 hours. The mixture is cooled to room temperature and most of the pyridine is removed in vacuo. The residue is treated with $CH_2Cl_2$ and saturated $NaHCO_3$ (aqueous solution). The organic layer is separated and the aqueous layer is extracted with $CH_2Cl_2$. The combined organic layer is dried ($Na_2SO_4$) and the solvent is removed in vacuo. The residue is purified by column chromatography on silica gel to give 3.

A solution of compound 3 and anhydride 4 in DMSO is heated at 65° C. (bath temperature) under $N_2$ for 16 hours. The mixture is allowed to cool to room temperature and is treated with 1:1 mixture of ether and ethyl acetate. This is washed with brine followed by water and then dried with $Na_2SO_4$. The solvent is removed in vacuo and the residue is purified by column chromatography on silica gel to give compound 5. This is recrystallized from and dried in vacuum oven at 65° C. overnight to give 5.

Example 2

Synthesis of PPAT Inhibitor Compound 6

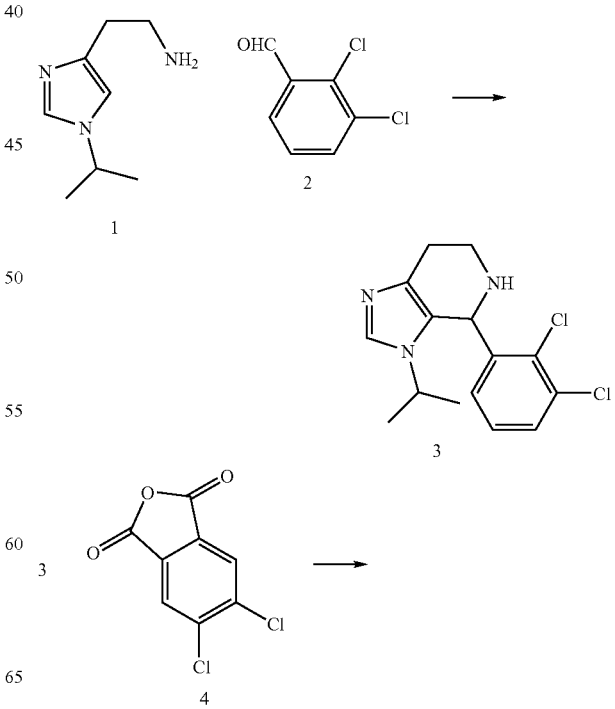

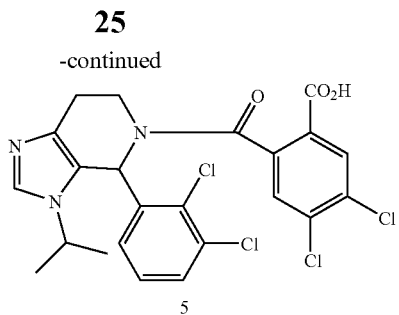

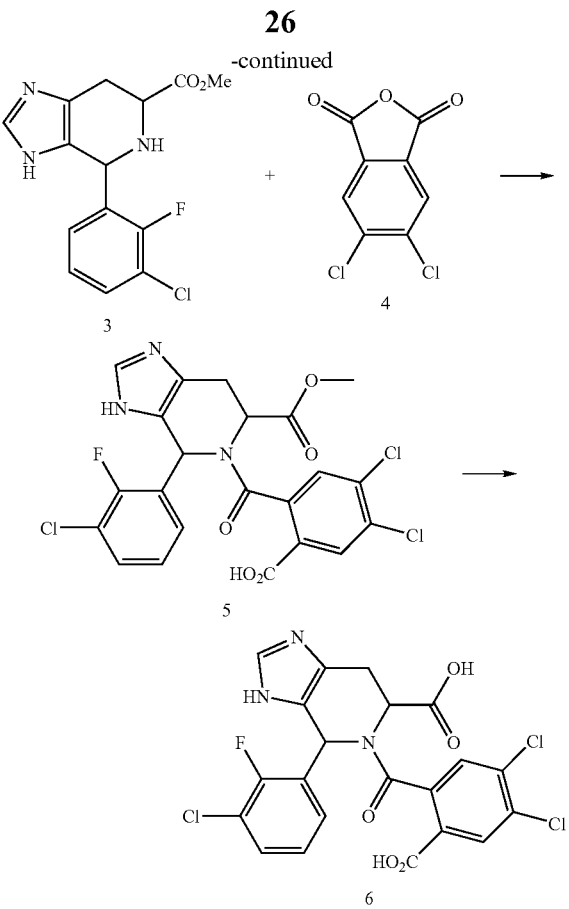

A mixture of amine bis-hydrochloride 1 (502 mg, 2.22 mM), anhydrous sodium acetate (240 mg, 2.92 mM) and aldehyde 2 (398 mg, 2.27 mM) in pyridine (20 mL) was heated to reflux under $N_2$ for 16 hours. The mixture was cooled to room temperature and most of the pyridine was removed in vacuo. The residue was treated with $CH_2Cl_2$ (100 mL) and saturated $NaHCO_3$ aqueous solution (50 mL). The organic layer was separated and the aqueous layer was extracted with $CH_2Cl_2$ (1×100 mL, 2×30 mL). The combined organic layer was dried ($Na_2SO_4$) and the solvent was removed in vacuo. The residue was purified by column chromatography on silica gel (ethyl acetate~ethyl acetate/methanol 95: 5) to give 3 as a off-white waxy solid (386 mg, 56%). (NMR of parent compound: $^1$HNMR 2.58(2H, $CH_2$—$CH_2NH$), 2.82 (2H, $CH_2$—$CH_2$—NH), 5.30 (1H, ArCH—NH), 6.92 (1H, 6-phenyl proton), 7.22 (1H, 5-phenyl proton), 7.42 (1H, imidazole proton), 7.55 (1H, 5-phenyl proton)).

A solution of compound 3 (150 mg, 0.48 mM) and anhydride 4 (111 mg, 0.48 mM) in DMSO (10 mL) was heated at 65° C. (bath temperature) under $N_2$ for 16 hours. The mixture was allowed to cool to room temperature and was treated with 300 mL (ether/ethylacetate:1/1). This was washed with brine (2×50 mL) followed by water (3×50 mL) and then dried ($Na_2SO_4$). The solvent was removed in vacuo and the residue was purified by column chromatography on silica gel (ethyl acetate/hexane: 4/2 to 1/0) to give compound 5. This was recrystallized from chloroform/hexane and dried in vacuum oven at 65° C. overnight to give 5 as white powder (108 mg, 42%). $^1$H NMR (dmso-$d_6$): was not well defined due to rotomers. MS: m+1=526 and m−1=524.

A mixture of L-histidine methyl ester dihydrochloride (506 mg, 2.09 mM), anhydrous sodium acetate (206 mg, 2.51 mM) and aldehyde 2 (360 mg, 2.27 mM) in pyridine (25 mL) was heated to reflux under nitrogen for 64 hours. The mixture was cooled to room temperature and most of the pyridine was removed in vacuo. The thick dark residue was treated with $CH_2Cl_2$ (100 mL) and water (100 mL) and the resulting mixture was stirred vigorously for one hour. The organic layer was separated and the aqueous was extracted with $CH_2Cl_2$ (3×50 mL). The combined organic layer was dried ($Na_2SO_4$) and the solvent was removed in vacuo and brown residue was purified by column chromatography to silica gel (ethyl acetate/methanol/triethylamine 100/10/1) to give compound 3 (295 mg, 45%) as a off-white solid. Compound 5 was prepared from 3 and anhydride 4 in 55% yield.

To a solution of 5 (125 mg, 0.23 mM) in THF—$H_2O$ (9:1) was added LiOH—$H_2O$ (38 mg, 0.90 mM) under $N_2$ and the resulting mixture was stirred for 20 hours. Most of the THF was removed in vacuo and the residue was treated with water (2 mL). This was treated with citric acid (200 mg) with vigorous stirring for 1 hour. The white ppt was filtered and washed with water and then dried in vacuum oven at 65° C. for 60 hours to give 6 as colorless solid (81 mg, 68%). MS: M+1=512

Example 3

Synthesis of PPAT Inhibitor: Racemate of Compounds 11 and 12

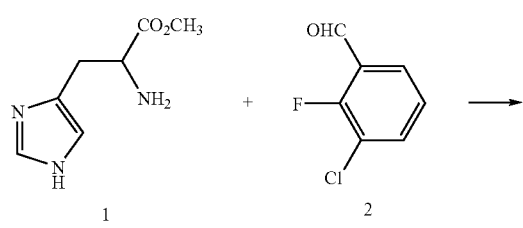

Example 4

Bacteria are Dependent on PPAT, a General Target for Antibiotics

The gene for PPAT, named coaD (alternatively, kdtE), has been identified: see Geerlof, et al., "Purification and characterization of Phosphopantetheine Adenylyltransferase from *E. Coli*" J. Biol. Chem., 1999, 274(38), pp. 27105-11, the entire teachings of which are incorporated herein by reference. The gene sequence has been searched in a range of bacteria and in mammals using BLAST® (Basic Local Alignment Search Tool, available online at http://www.ncbi.nkri.nih.gov/BLAST/). The results are provided in Table 2.

TABLE 2

Conservation of PPAT gene (coaD) among range of bacterial species

| Bacteria | Gram p/n | P(N) | % Identity | % Similarity |
|---|---|---|---|---|
| *Klebsiella pneumoniae* | negative | 1.4E−72 | 85 | 91 |
| *Pseudomonas aeruginosa* | negative | 7.20E−49 | 61 | 81 |
| *Neisseria meningitidis* | negative | 4.80E−27 | 35 | 62 |
| *Enterococcusfaecium* | positive | 4.20E−36 | 46 | 67 |
| *Staphylococcus aureus* | positive | 2.10E−36 | 46 | 69 |
| *Staphylococcus* | positive | 1.10E−35 | 44 | 67 |
| *Streptococcus* | positive | 2.60E−26 | 36 | 61 |
| (mammalian) | NA | — | 18 | — |

PPAT is seen to be highly conserved across a range of bacterial pathogens. Thus, PPAT is a general target for antibiotics. Furthermore, although PPAT is present in mammalian cells, the mammalian sequence is sufficiently different to indicate that the disclosed PPAT inhibitors can be selective for bacterial PPAT.

The gene for PPAT, coaD, is disrupted from a range of bacteria by allelic exchange; see, for example, Geerlof, et al., above, and Freiberg, et al. 2001. "Identification of novel essential *Escherichia coli* genes conserved among pathogenic bacteria" J Mol Microbiol Biotechnol 2001, 3, pp 483-9, the entire teachings of which are incorporated herein by reference. The survival of *Escherichia coli, Bacillus subtilis, Staphylococcus aureus*, and *Streptococcus pneumoniae* in complex growth media is studied. The inability of the modified bacteria to survive without the coaD gene indicates that PPAT is necessary for bacterial survival and is thus a potential antibiotic target.

An additional experiment can test the survival of *Escherichia coli* in media containing exogenous dePhospho-CoA and/or CoA. Mammalian, including human cells, can make CoA from pantothenate (vitamin $B_5$) scavenged from the environment. Thus, it is possible that in a human subject, human cells/tissues could supply CoA to a bacterium that is unable to synthesize CoA. The inability of modified *Escherichia coli* to survive in media containing exogenous dePhospho-CoA and/or CoA further indicates that PPAT can be an antibacterial target.

Example 5

Kinetic Assay of PPAT Inhibition

The $IC_{50}$ (Inhibition Concentration at 50 percent) values for the disclosed compounds against PPAT can be determined with various concentrations of the compounds in a range of 0.003~200 μg/ml. Compounds with $IC_{50}$ values >200 can have a measurable IC50 using a different assay method. These inhibition assays can be performed in 96-well assay plates, using a similar method to the screening assay above. The reaction buffer should contain 20 mM Hepes (pH 7.5), 100 mM NaCl, 1 mM $MgCl_2$, 0.5 mM DTT, 0.006% Brij 35, 10% Glycerol, 25 μM PPT, 0.5 mM ATP, 0.2 Unit of pyrophosphatase, 200 ng of PPAT in a total volume of 100 μl. The reaction is performed for 2 minutes, and then stopped with 150 ml Malachite Green reagent. Absorption at 650 nm is measured after 10 minutes of color development. The $IC_{50}$'s are determined with fitting data to the four-parameter method using XLfit (ID Business Solutions Inc., Cambridge, Mass.). The $IC_{50}$ value is derived from the curve as the compound concentration that gives 50% inhibition of the enzymatic reaction.

In order to perform the $IC_{50}$ assays, purified PPAT is needed. The *E. coli* PPAT gene is cloned into the pET28a expression vector (Novagen, Inc., Madison, Wis.) and expressed in *E. coli* BL21(DE3) cells. A chromatographic purification procedure employs Q-sepharose, gel filtration, and MonoQ chromatography, as follows. The methods are described in detailed in Geerlof, et al., above.

Each cell pellet is suspended in a 4 fold-volume of lysis buffer (50 mM $KH_2PO_4$ pH 8.0, 100 mM NaCl, 2 mM EGTA, and 10% glycerol. Cells are broken by passage through a Microfluidics cell disrupter 4 times, and the cell lysate should be centrifuged at 3,000 g for 20 minutes. The supernatant is then applied to a pre-equilibrated Q-sepharose column (10 mM Tris-HCl pH 8.0, 0.1 mM EGTA, 1 mM PMSF, 100 mM NaCl, 10% glycerol, 0.1% p-mercaptoethanol, and 0.02% Brij 35). PPAT is eluted with NaCl gradient (0.1-1M) in the equilibrium buffer. The major peak fractions are pooled and concentrated, then applied to a Sephacryl S200 HR column (10 mM Tris-HCl pH 7.5, 150 mM NaCl, 0.1 mM EGTA, 0.1 mM PMSF, 10% glycerol, 0.1% β-mercaptoethanol, and 0.02% Brij 35). PPAT is eluted with the same buffer. The major peak fractions are pooled and loaded on a pre-equilibrated MonoQ column (10 mM Tris-HCl, pH 7.0, 0.1 mM EGTA, 0.1 mM PMSF, 10% glycerol, 0.1% β-mercaptoethanol, and 0.02% Brij 35). PPAT should be eluted with a gradient of NaCl from 100 mM up to 1000 mM. The peak fractions are pooled and dialyzed in the storing buffer (10 mM MOPS pH7.0, 150 mM NaCl, 0.1 mM EGTA, 50% glycerol, 0.02% Brij 35), then stored at −20° C. Results from these experiments for compounds of the current invention are shown in Table 3.

TABLE 3

Disclosed compounds are inhibitors of PPAT

| Compound # | PPAT *E. Coli* $IC_{50}$ |
|---|---|
| 1 | >200 μM |
| 2 | >200 μM |
| 3 | >200 μM |
| 4 | >200 μM |
| 5 | >200 μM |
| 6 | 40-70 μM |
| 7 | >200 μM |
| 8 | >200 μM |
| 9 | >200 μM |
| 10 | >200 μM |
| 11 | >200 μM |
| 12 | >200 μM |
| 13 | 65-100 μM |
| 14 | 100-200 μM |
| 15 | 25-75 μM |
| 16 | 100-200 μM |

Example 6

Measuring Disclosed PPAT Inhibitors' Antibiotic Activity Against Drug-Resistant Bacteria Potency, spectrum, target specificity and serum effect is evaluated by measuring the MIC (Minimum Inhibitory Concentration). This is the lowest concentration, in μg/mL, in a series of 2-fold dilutions of the compound that completely inhibits growth, for a panel of pathogenic bacteria. The strains comprising the bacterial panel are either obtained from American Type Culture Collection (ATCC, Manassas, Va.), or genetically engineered to express varying levels of PPAT. The ATCC strains include the following: *Escherichia coli* (ATCC 35218), *Staphylococcus aureus* (ATCC 700699), and *Enterococcusfaeciim* (ATCC 700221). Other strains include *Staphylococcus aureus* RN4220, *Escherichia coli* WO-0159, *Escherichia coli* WO-0153, and *Bacillus subtilis* BD170 with endogenous PPAT disrupted and complemented with PPAT under the regulation of inducible promoter, $P_{space}$.

The MIC assays are performed essentially as described in the NCCLS recommendations, the entire teachings of which are incorporated herein by reference (National Center for Clinical Laboratory Standards, 1997, (Methods for Dilution Antimicrobial Susceptibility Tests for Bacteria the Grow Aerobically), 4th ed.; approved standard. NCCLS document M7-A4. NCCLS, Wayne, Pa.), with the following exceptions: both Tryptic Soy broth, and Mueller Hinton broth with and without the presence of serum are used as the growth medium. The concentration range tested is from 200 to 0.39 mcg/ml. Concentrations of 50-fold the desired final concentration are made by 2-fold serial dilutions in 96-well microtiter plates, after which 2 μL are transferred to the assay plates. Cells are grown up in the appropriate culture media and diluted back to final $OD_{600}$ of 0.001, after which 98 μL is inoculated into the assay plates. The final volume in each assay well is 100 uL. After an overnight incubation at 37° C., the assay plates are read. The MIC is determined as the minimal concentration that results in >80% inhibition of growth.

The invention claimed is:
1. A compound represented by structural Formula I:

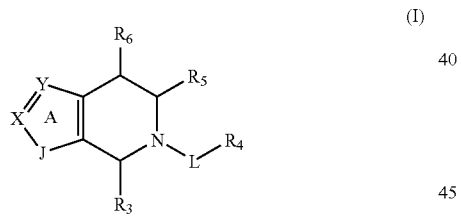

(I)

and pharmaceutically acceptable salts, enantiomers, stereoisomers, rotamers, tautomers, diastereomers, or racemates thereof;
ring A is an optionally substituted furanyl, pyrrolyl, thienyl, oxazolyl, isooxazolyl, thiazolyl, isothiazolyl, or imidazolyl group;
X and Y are each, independently, —C— or —N—;
J is —O—, —S—, or —$NR_2$—, wherein $R_2$ is —H or optionally substituted C1-C5 alkyl;
or, J is —$NR_2'$—, wherein $R_2'$ is optionally substituted aryl, aralkyl, heteroaryl, heteroaralkyl, C3-C7 cycloaliphatic, or C3-C7 cycloalkyl;
wherein ring A is optionally substituted at any substitutable ring atom with $R_1$, wherein each $R_1$ is independently halogen, —CN, —$NO_2$, —$OR^d$, —$(CO)R^d$, —(CO)$OR^d$, —$O(CO)R^d$, —$(CO)O(CO)R^d$, —$(CS)OR^d$, —$(SO)OR^d$, —$SO_3R^d$, —$CONR^e_2$, —$O(CO)NR^e_2$, —$NR^f(CO)NR^e_2$, —$NR^f(CO)OR^d$, —$NR^fCOR^d$, —$(SO_2)NR^e_2$, —$NR^fSO_2R^d$, —$(CH_2)_sNR^d_2$, or optionally substituted aryl, aralkyl or C1-C5 alkyl;

wherein:
each $R^d$ and $R^f$ are, independently, —H, aryl, aralkyl, C1-C5 alkyl, or C1-C5 haloalkyl; and
each $R^e$ is independently —H, aryl, aralkyl, or C1-C5 alkyl, or $NR^e_2$ is a nonaromatic heterocyclic group, and s is 0 to 5;
$R_3$ is optionally substituted phenyl, pyridyl, benzol[1,3]dioxolyl, 2,3-dihydro-benzol[1,4]dioxine, pyrimidyl, pyrazyl, furanyl, pyrrolyl, thienyl, oxazolyl, isooxazolyl, thiazolyl, isothiazolyl, imidazolyl, naphthyl, quinolinyl, biphenyl, benzopyrimidyl, benzopyrazyl, benzofuranyl, indolyl, benzothienyl, benzoxazolyl, benzoisooxazolyl, benzothiazolyl, benzoisothiazolyl, or benzimidazolyl group;
L is —($CH_2$)—, —(CO)—, —(CS)—, —(SO)—, or —($SO_2$)—;
$R_4$ is represented by one of structural formulas R4-i to R4-vii;

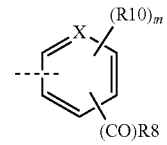

R4-i

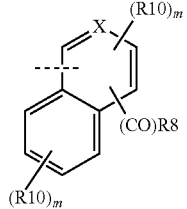

R4-ii

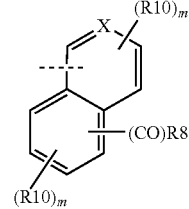

R4-vi

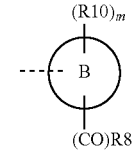

R4-iii

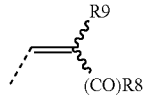

R4-iv

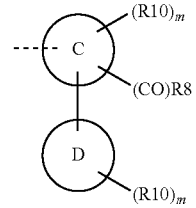

R4-v

-continued

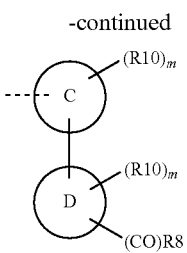
R4-vii wherein:
each m is independently 0, 1, 2, or 3;
X is —N—, —CH—, or —CR$_{10}$—;
Ring B is C3-C6 cycloalkyl or C3-C6 cycloalkenyl;
Rings C and D are each independently aryl or heteroaryl;
R$_8$ is —OR$^q$ or —NR$^r_2$;
R$_9$ is —H, aryl, aralkyl, or C1-C6 aliphatic;
each R$_{10}$ is independently halogen, —CN, —NO$_2$, —CF$_3$, —OCF$_3$, —OR$^i$, —(CO)R$^i$, —(CO)OR$^i$, —O(CO)R$^i$, —(CO)O(CO)R$^i$, —(CS)OR$^i$, —(SO)OR$^i$, —SO$_3$R$^i$, —CONR$^j_2$, —O(CO)NR$^j_2$, —NR$^k$(CO)NR$^j_2$, —NR$^k$(CO)OR$^i$, —NR$^k$COR$^i$, —(SO$_2$)NR$^j_2$, —NR$^k$SO$_2$R$^i$, —(CH$_2$)$_t$NR$^j_2$, or optionally substituted aryl, aralkyl or C1-C5 alkyl;
each R$^i$ and R$^k$ are, independently, —H, aryl, aralkyl, C1-C5 alkyl, or C1-C5 haloalkyl;
each R$^j$ and R$^r$ are, independently, —H, aryl, aralkyl, or C1-C5 alkyl, or each NR$^j_2$ and NR$^r_2$ are, independently, a nonaromatic heterocyclic group;
R$^q$ is —H or optionally substituted aryl, aroyl, aralkyl, aralkanoyl, C1-C5 alkyl, or C1-C5 alkanoyl; and
t is 0 to 5;
R$_5$ is —H, —(CH$_2$)$_n$(CO)OR$^a$, —(CH$_2$)$_n$(CO)O(CO)R$^a$, —(CH$_2$)$_n$(CS)OR$^a$, —(CH$_2$)$_n$(SO)OR$^a$, —(CH$_2$)$_n$SO$_3$R$^a$, —(CH$_2$)$_n$OSO$_3$R$^a$, —(CH$_2$)$_n$P(OR$^a$)$_2$, —(CH$_2$)$_n$(PO)(OR$^a$)$_2$, —(CH$_2$)$_n$O(PO)(OR$^a$)$_2$, —(CH$_2$)$_n$B(OR$^a$)$_2$, —(CH$_2$)$_n$(CO)NR$^b_2$, —(CH$_2$)$_n$NR$^c$(CO)R$^a$, —(CH$_2$)$_n$SO$_2$NR$^b_2$, or —(CH$_2$)$_n$NR$^c$SO$_2$R$^a$;
R$_6$ is —H, —OH, halogen, or optionally substituted C1-C3 alkyl or alkoxy;
n is 0 to 5;
each R$^a$ and R$^c$ are, independently, —H, C1-C5 alkyl, aryl, or aralkyl;
each R$^b$ is, independently, —H, C1-C5 alkyl, aryl, or aralkyl, or NR$^b_2$ is a nonaromatic heterocyclic group.

2. The compound of claim 1, wherein R$_4$ is represented by one of structural formulas R4-i' to R4-vii':

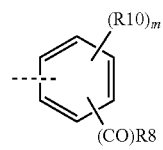
R4-i'

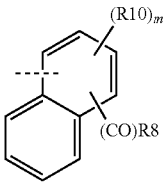
R4-ii'

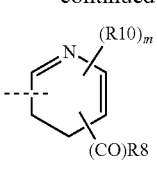
R4-iii'

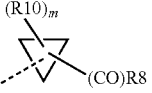
R4-iv'

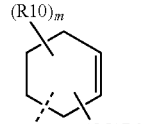
R4-v'

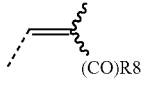
R4-vi'

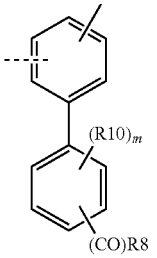
R4-vii' wherein:
each m is independently 0, 1, 2, or 3;
R$_8$ is —OH, C1-C5 alkoxy, or C1-C0 alkanoyloxy;
R$_9$ is —H or C1-C6 aliphatic; and
each R$_{10}$ is independently —OH, —NO$_2$, —F, —Cl, —Br, C1-C4 alkyl, C1-C4 alkoxy, —CF$_3$, or —OCF$_3$.

3. The compound of claim 1, wherein R3 is represented by one of structural formulas R3-i to R3-v:

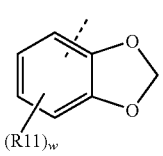
R3-i

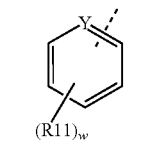
R3-ii

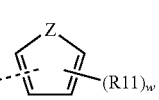
R3-iii

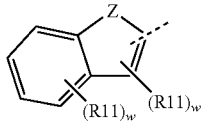
R3-iv

-continued

R3-v

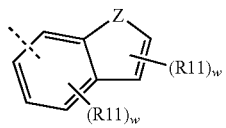

wherein

Y is —N—, —CH—, or —CR₁₁—;

Z is —NR$^z$—, —S—, or —O—, wherein R$^z$ is —H or C1-C3 alkyl;

the variable w is 0, 1, 2, or 3;

each R₁₁ are, independently, halogen, —CN, —NO₂, —CF₃, —OCF₃, —OR¹, —(CO)R¹, —(CO)OR¹, —O(CO)R¹, —(CO)O(CO)R¹, —(CS)OR¹, —(SO)OR¹, —SO₃R¹, —CONR$^m$₂, —O(CO)NR$^m$₂, —NR$^n$(CO)NR$^m$₂, —NR$^n$(CO)OR¹, —NR$^n$COR¹, —(SO₂)NR$^m$₂, —NR$^n$SO₂R¹, —(CH₂)ᵤNR¹₂, or optionally substituted aryl, aralkyl, or C1-C5 alkyl;

u is 0 to 5, each R¹ and R$^n$ are, independently, —H, aryl, or aralkyl, C1-C5 alkyl, or C1-C5 haloalkyl; and each R$^m$ is independently —H, aryl, aralkyl, or C1-C5 alkyl, or NR$^m$₂ is a nonaromatic heterocyclic group.

4. The compound of claim 3 wherein R₃ is represented by one of structural formulas R3-i' to R3-v':

R3-i'

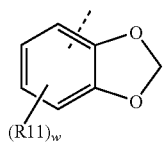

R3-ii'

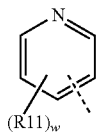

R3-iii'

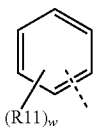

R3-iv'

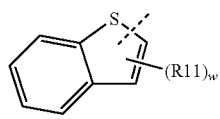

R3-v'

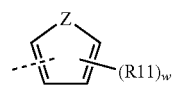

wherein:

w is 0, 1, 2, or 3; and each R₁₁ is independently —OH, —NO₂, —F, —Cl, —Br, C1-C4 alkyl, C1-C4 alkoxy, —CF₃, or —OCF₃.

5. A compound represented by structural Formula I:

(I)

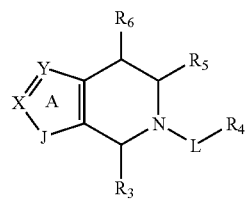

and pharmaceutically acceptable salts, enantiomers, stereoisomers, rotamers, tautomers, diastereomers, or racemates thereof;

ring A is optionally substituted at any substitutable ring atom;

X and Y are each, independently, —C— or —N—;

J is —O—, —S—, or —NR2—, wherein R2 is —H or optionally substituted C1-C5 alkyl;

or, J is —NR₂'—, wherein R₂' is optionally substituted aryl, aralkyl, heteroaryl, heteroaralkyl, C3-C7 cycloaliphatic, or C3-C7 cycloalkyl;

R₃ is optionally substituted aryl, aralkyl, heteroaryl, heteroaralkyl, C3-C7 cycloaliphatic, or C3-C7 cycloalkyl;

L is —(CH₂)—, —(CS)—, —(SO)—, or —(SO₂)—;

R₅ is —H, —(CH₂)ₙ(CO)OR$^a$, —(CH₂)ₙ(CO)O(CO)R$^a$, —(CH₂)ₙ(CS)OR$^a$, —(CH₂)ₙ(SO)OR$^a$, —(CH₂)ₙSO₃R$^a$, —(CH₂)ₙOSO₃R$^a$, —(CH₂)ₙ(OR$^a$), —(CH₂)$^n$(PO)(OR$^a$, —(CH₂)ₙO(PO)(OR$^a$)₂, —(CH₂)ₙB(OR$^a$)₂, —(CH₂)ₙ(CO)NR$^b$₂, —(CH₂)ₙNR$^c$(CO)R$^a$, —(CH₂)ₙSO₂NR$^b$₂, or —(CH₂)ₙNR$^c$SO₂R$^a$;

R₆ is —H, —OH, halogen, or optionally substituted C1-C3 alkyl or alkoxy;

n is 0 to 5;

each R$^a$ and R$^c$ are, independently, —H, C1-C5 alkyl, aryl, or aralkyl;

each R$^b$ is, independently, —H, C1-C5 alkyl, aryl, or aralkyl, or NR$^b$₂ is a nonaromatic heterocyclic group;

R₈ is —OR$^q$ or —NR$^r$₂;

each R$^r$ is, independently, —H, aryl, aralkyl, or C1-C5 alkyl, or NR$^r$₂ is, independently, a nonaromatic heterocyclic group;

R$^q$ is —H or optionally substituted aryl, aroyl, aralkyl, aralkanoyl, C1-C5 alkyl, or C1-C5 alkanoyl;

R₄ is represented by one of structural formulas R4$^a$ to R4$^q$:

R4$^a$

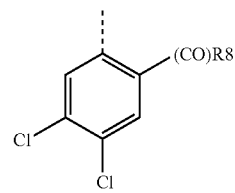

R4$^b$

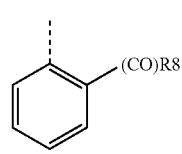

-continued
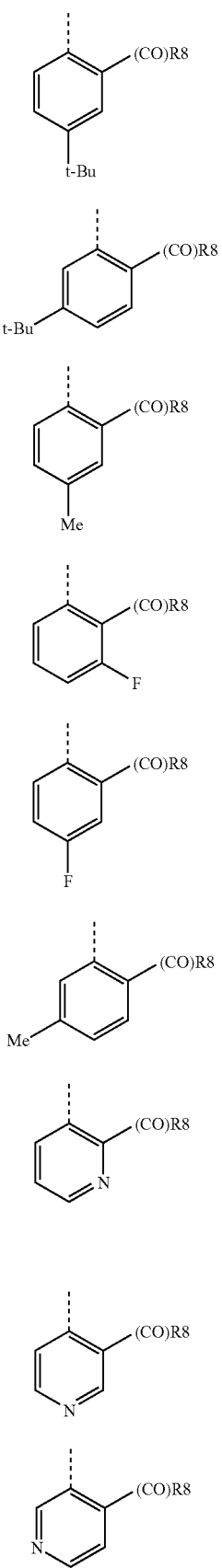
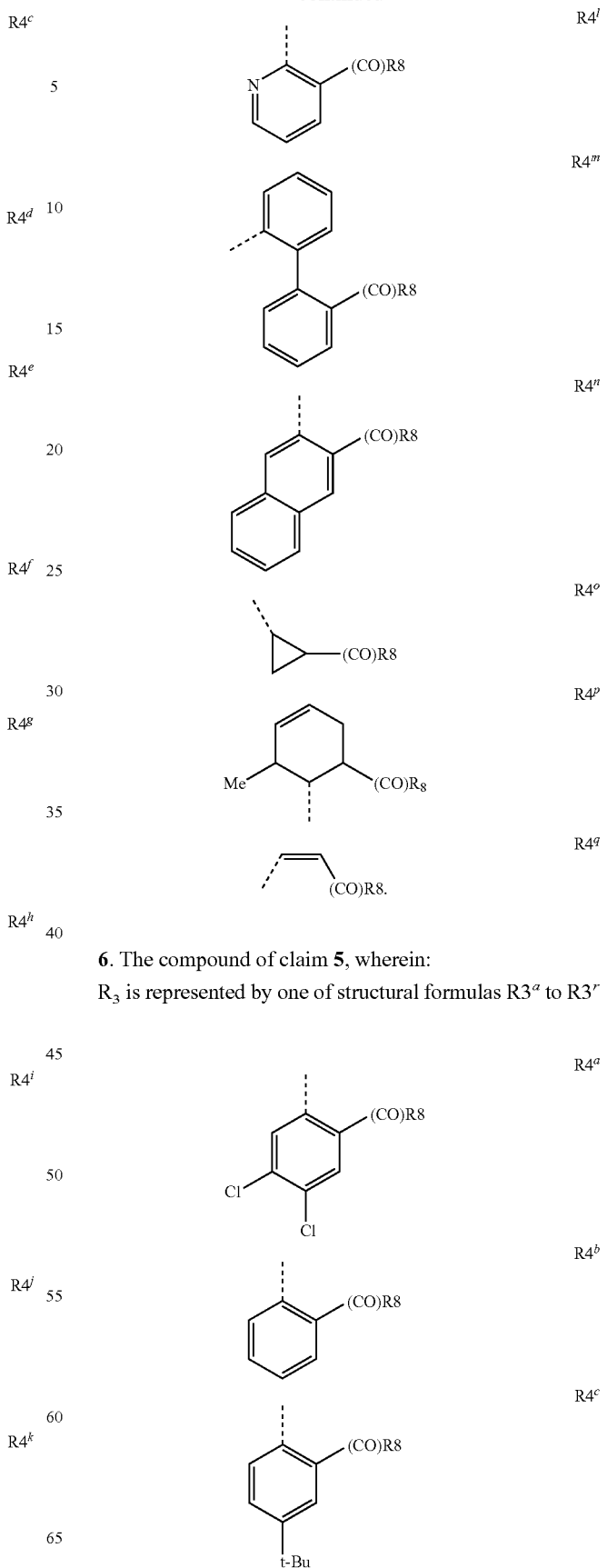
6. The compound of claim 5, wherein:
R₃ is represented by one of structural formulas R3$^a$ to R3$^r$
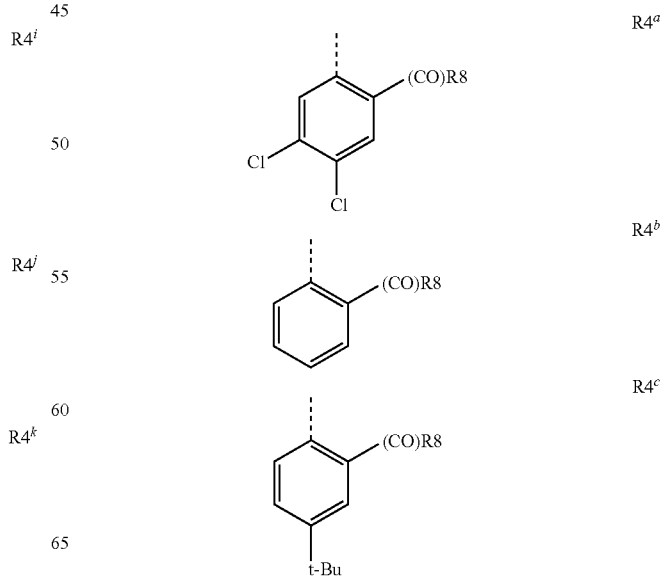

-continued

R4$^d$ 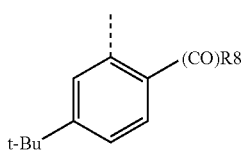

R4$^e$ 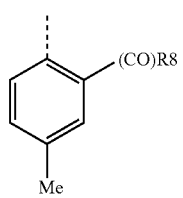

R4$^f$ 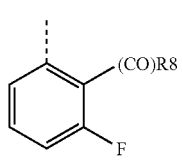

R4$^g$ 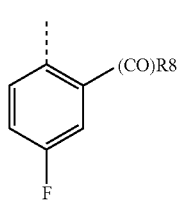

R4$^h$ 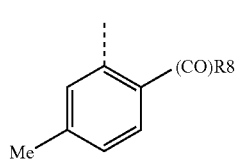

R4$^i$ 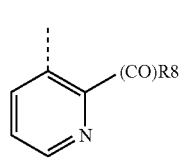

R4$^j$ 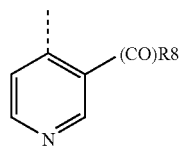

R4$^k$ 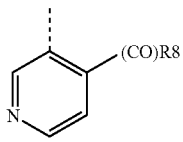

R4$^l$ 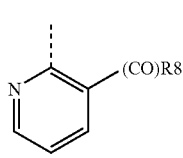

-continued

R4$^m$ 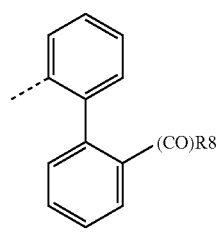

R4$^n$ 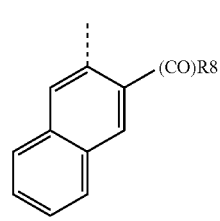

R4$^o$ 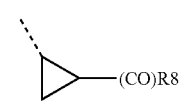

R4$^p$ 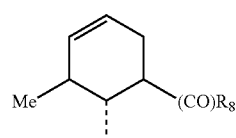

R4$^q$ 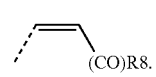

7. A compound represented by structural Formula I:

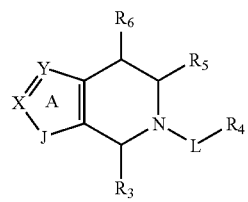

(I)

and pharmaceutically acceptable salts, enantiomers, stereoisomers, rotamers, tautomers, diastereomers, or racemates thereof;

wherein ring A is an imidazole moiety that is optionally substituted one or more times with C1-C4 alkyl;

$R_3$ is phenyl optionally substituted one or more times with halogen;

L is —(CO)—;

$R_4$ is phenyl optionally independently substituted one or more times with halogen and —CO$_2$H;

$R_5$ is —CO$_2$H; and, $R_6$ is —H, —OH, halogen, or optionally substituted C1-C3 alkyl or alkoxy.

8. A compound of formula 5:

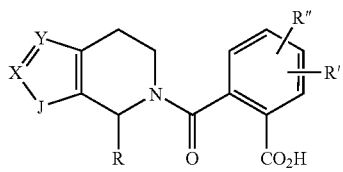

and pharmaceutically acceptable salts, enantiomers, stereoisomers, rotamers, tautomers, diastereomers, or racemates thereof;

wherein:

R is optionally substituted aryl, aralkyl, heteroaryl, heteroaralkyl, C3-C7 cycloaliphatic or C3-C7 cycloalkyl; and, R' and R" are each independently hydrogen, halogen, alkyl or alkoxy;

Y is —N— or —CH— or —C—;

J is —NH—, —O— or —S—; and

X is —C—.

9. A compound of formula 6:

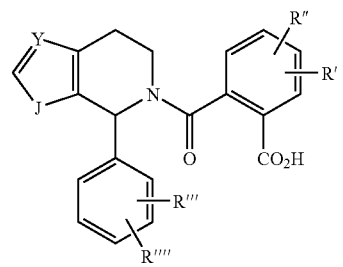

and pharmaceutically acceptable salts, enantiomers, stereoisomers, rotamers, tautomers, diastereomers, or racemates thereof;

wherein R' and R" are each, independently, hydrogen, alkyl or halogen;

R''' and R'''' are each, independently, hydrogen, alkoxy or halogen; and

Y and J are each, independently, —S— or —N—.

10. The compound of claim 1, wherein the compound of Formula I is selected from the group consisting of compounds 1-16:

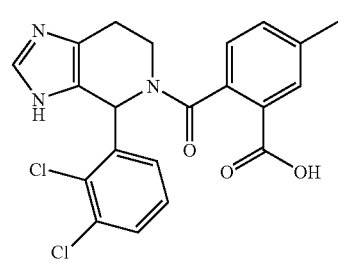

1

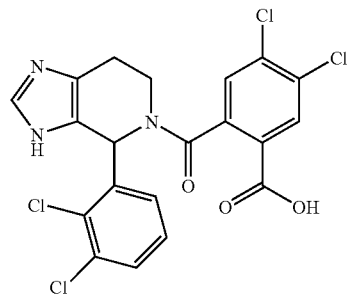

2

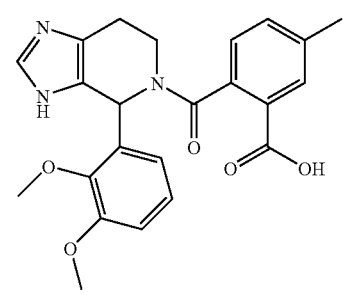

3

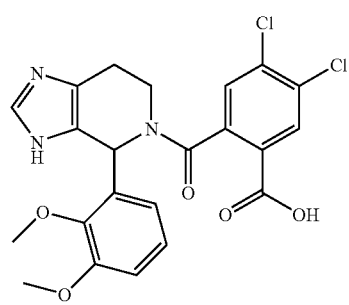

4

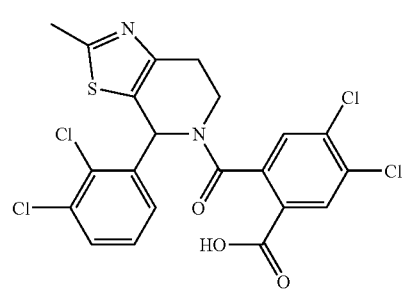

5

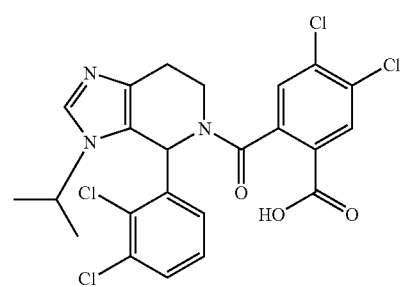

6

-continued
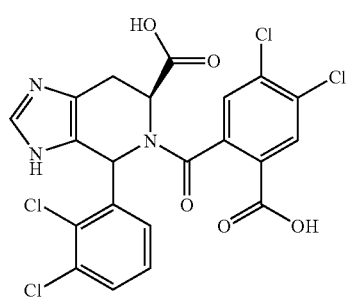
7
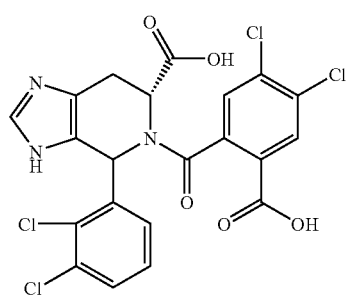
8
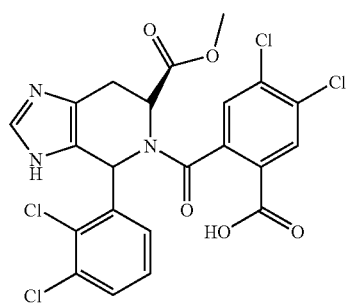
9
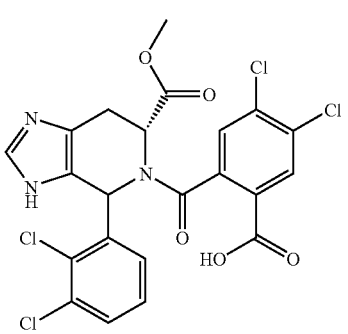
10
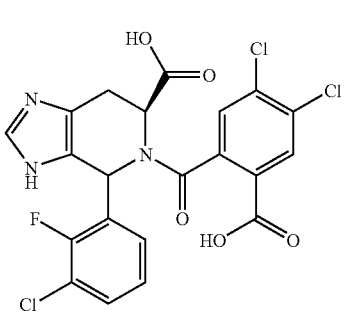
11
-continued
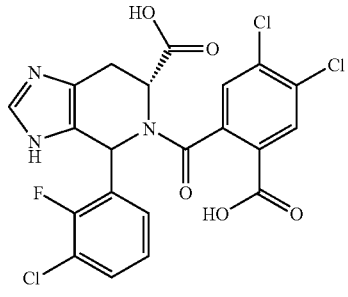
12
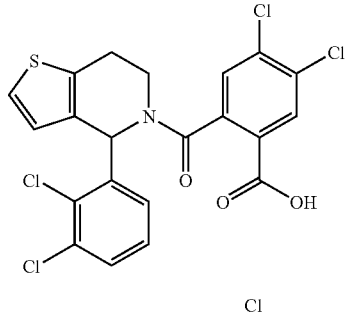
13
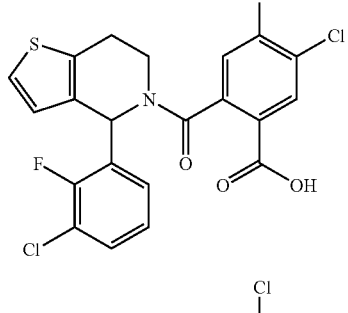
14
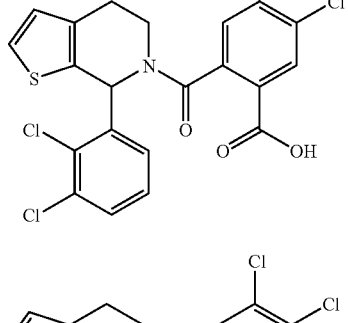
15
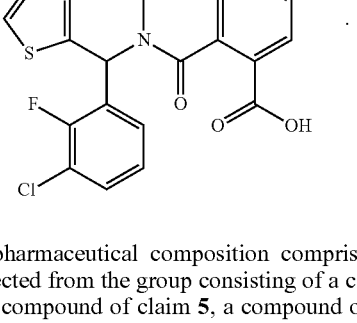
16
11. A pharmaceutical composition comprising a compound selected from the group consisting of a compound of claim 1, a compound of claim 5, a compound of claim 7, a compound of claim 8, and a compound of claim 9.
* * * * *